(12) United States Patent
Komase et al.

(10) Patent No.: US 7,208,163 B1
(45) Date of Patent: Apr. 24, 2007

(54) METHOD FOR PRODUCING TEMPERATURE-SENSITIVE MORBILLIVIRUS

(75) Inventors: Katsuhiro Komase, Tokyo (JP); Noriko Suzuki, Tokyo (JP); Tetsuo Nakayama, Tokyo (JP); Chikara Aizawa, Saitama (JP)

(73) Assignee: The Kitasato Institute, Tokyo (JP)

( * ) Notice: Subject to any disclaimer, the term of this patent is extended or adjusted under 35 U.S.C. 154(b) by 0 days.

(21) Appl. No.: 10/203,703

(22) PCT Filed: Oct. 18, 2000

(86) PCT No.: PCT/JP00/07234

§ 371 (c)(1),
(2), (4) Date: Nov. 5, 2002

(87) PCT Pub. No.: WO01/59125

PCT Pub. Date: Aug. 16, 2001

(30) Foreign Application Priority Data

Feb. 10, 2000 (JP) ............................... 2000-38264

(51) Int. Cl.
*A61K 39/155* (2006.01)
*A61K 39/165* (2006.01)
(52) U.S. Cl. ................ 424/211.1; 424/212.1; 424/213.1; 435/69.1
(58) Field of Classification Search ............. 424/211.1; 435/69.1, 320.1; 536/23.1
See application file for complete search history.

(56) References Cited

U.S. PATENT DOCUMENTS 5,654,136 A 8/1997 Sasaki et al.
5,824,777 A 10/1998 Sasaki et al.

FOREIGN PATENT DOCUMENTS

JP 0540135 A2 * 5/1993

OTHER PUBLICATIONS

Sasaki, Keiko, Studies on the Modification of the Live AIK Measles Vaccine, Kitasato Archives of Experimental Medicine, 47(1-2):1-12, 1974.*
Bellini et al., "Measles virus P gene codes for two proteins," *J. Virol.*, 53(3):908-919 (1985).
Komase et al., "Sendai virus C proteins are categorically nonessential gene products but required for viral assembly," (1999).
Mori et al., "Molecular cloning and complete nucleotide sequence of genomic RNA of the AIK-C strain of attenuated measles virus," *Virus Genes*, 7(1):67-81 (1993).
Vydelingum et al., "Infection of human peripheral blood mononuclear cells with a temperature-sensitive mutant of measles virus," *J. Virol.*, 63(2):689-695 (1989).

* cited by examiner

*Primary Examiner*—Stacy B. Chen
(74) *Attorney, Agent, or Firm*—Townsend and Townsend and Crew LLP

(57) ABSTRACT

It was found that a mutation of an amino acid at a specific position in the P protein of a morbillivirus gives a temperature-sensitivity character to a virus. By introducing this mutation, a virus to which a temperature-sensitivity character has been introduced can be produced. According to this invention, attenuated viruses useful in the preparation of vaccines can be easily produced.

53 Claims, 8 Drawing Sheets

Fig. 8

```
AIK-C P protein          1 MAEEQARHVKNGLECIRALKAEPIGSLAIEEAMAAWSEISDNPGQERATCREEKAGSSGL  60
Edmonston P protein      1 MAEEQARHVKNGLECIRALKAEPIGSLAIEEAMAAWSEISDNPGQERATCREEKAGSSGL  60
CDV P protein            1 MAEEQAYHVSKGLECLKALRENPPDIEEIQEVSSLRDQTCNPGQENGTTGMQEEEDSQNL  60
PDV P protein            1 MAEEQAYHVSKGLECIKALRENPPNMEEIQEVSNIRDQTYKSSKESGTTGVQEEEITQNI  60
Rinderpest P protein     1 MAEEQAYHVNKGLECIKALRARPLDPLVVEEALAAWVETSEGQTLDRMSSDEAEADHQDI  60

AIK-C P protein         61 SKPCLSAIGSTEGGAPRIRGQGPGESDDDAETLGIPPRNLQASSTGLQCYYVYDHSGEAV 120
Edmonston P protein     61 SKPCLSAIGSTEGGAPRIRGQGPGESDDDAETLGIPPRNLQASSTGLQCDYVYDHSGEAV 120
CDV P protein           61 DESHEPTKGSNYVGHVPQNNPGCGERNTALVEAERPPREDIQPGPGIRCDHVYDHSGEEV 120
PDV P protein           61 DESHTPTKRSNSVSDVLQEDQRGREDNTAPVEAKDRIEEDTQTGPAVRRYYVYDHCGEKV 120
Rinderpest P protein    61 SKPCFPAAGPGKSSMSRCHDQGLGGSNSCDEELGAFIGDSSMHSTEVQHYHVYDHSGEKV 120

AIK-C P protein        121 KGIQDADSIMVQSGLDGDSTLSGGDNESENSDVDIGEPDTEGYAITDRGSAPISMGFRAS 180
Edmonston P protein    121 KGIQDADSIMVQSGLDGDSTLSGGDNESENSDVDIGEPDTEGYAITDRGSAPISMGFRAS 180
CDV P protein          121 KGIEDADSLVVPAGTVGNRGFERGEGSLDDSTEDSGEDYSEGNASSNWGYSFGLKPDRAA 180
PDV P protein          121 KGIEDADSLMVPAGPPSNRGFEGREGSLDDSIEDSSEDYSEGNASSNWGYTFGLNPDRAA 180
Rinderpest P protein   121 EGVEDADSILVQSGADDGVEVWGGDEESENSDVDSGEPDPEGSAPADWGSSPISPATRAS 180

AIK-C P protein        181 DVETAEGGEIHELLRLQSRGNNFPKLGKTLNVPPPPDPGRASTSGTPIKKGTDARLASFG 240
Edmonston P protein    181 DVETAEGGEIHELLRLQSRGNNFPKLGKTLNVPPPPDPGRASTSGTPIKKGTDARLASFG 240
CDV P protein          181 DVSMLMEEELSALLRTSRNVGIQKRDGKTLQFPHNPEGKTRDPECGSIKKGTEERSVSHG 240
PDV P protein          181 DVSMLMEEELTTLLGTGHNAGGQKRDGRTLQFPNSPEGSIGNQVCEPIKKGTGEKLASHG 240
Rinderpest P protein   181 DVETVEGDEIQKLLEDQSRIRKMTKAGKTLVVPPIPSQERPTASEKPIKKGTDVKSTSSG 240

AIK-C P protein        241 TEIASLLTGGATQCARKSPSEPSGPGAPAGNVPEYVSNAALIQEWTPESGTTISPRSQNN 300
Edmonston P protein    241 TEIASLLTGGATQCARKSPSEPSGPGAPAGNVPECVSNAALIQEWTPESGTTISPRSQNN 300
CDV P protein          241 MGIVAGSTSGATQSALKSTGGSSEPSVSAGNVRQPAMNAKMTQKCKLESGTQLPPRTSNE 300
PDV P protein          241 MMTAAGLTNGATRSAPKSTGGSSGPNASAGSVPQSVTTAKMIQKCKTESGTRPQPEKPNE 300
Rinderpest P protein   241 TMAESSSTGGATRPALKSQWGPSGPNASAENALASASNVSPTQGSKTESGTTTSRISQSN 300

AIK-C P protein        301 EEGGDYYDDELFSDVQDIKTALAKIHEDNQKIISKLESLLLLKGEVESIKKQINRQNISI 360
Edmonston P protein    301 EEGGDYYDDELFSDVQDIKTALAKIHEDNQKIISKLESLLLLKGEVESIKKQINRQNISI 360
CDV P protein          301 AESDSEYDDELFSEIQEIRSAITKLTEDNQAILTKLDTLLLLKGETDSIKKQISKQNIAI 360
PDV P protein          301 IESDGEYDDELFSEIQEIRSAITKLTEDNQSILSKLDTLLLLKGEIDSIKKQISKQNIAI 360
Rinderpest P protein   301 IEPEDDYDDELFSDIQDIKTALAKLHDDQQIIITRLESLVSLKGEIDSIKKQISKQNISI 360

AIK-C P protein        361 STLEGHLSSIMIAIPGLGKDPNDPTADVEINPDLKPIIGRDSGRALAEVLKKPVASRQLQ 420
Edmonston P protein    361 STLEGHLSSIMIAIPGLGKDPNDPTADVEINPDLKPIIGRDSGRALAEVLKKPVASRQLQ 420
CDV P protein          361 STIEGHLSSIMIAIPGFGKDTGDPTANVDINPELRPIIGRDSGRALAEVLKQPASSRGNR 420
PDV P protein          361 STIEGHLSSIMIAIPGFGKDTGDPTANVDINPELRPIIGRDSGRALAEVLKKPASSRGNQ 420
Rinderpest P protein   361 STIEGHLSSVMIAIPGFGKDPNDPTADVDINPDLRPIIGRDSGRALAEVLKKPASERQSK 420
                                              439
AIK-C P protein        421 GMTNGRTSSRGQLLKEFQPKPIGKKMSSAVGFVPDTGPASRSVIRSIIKSSRLEEDRKRY 480
Edmonston P protein    421 GMTNGRTSSRGQLLKEFQLKPIGKKMSSAVGFVPDTGPASRSVIRSIIKSSRLEEDRKRY 480
CDV P protein          421 KDSGITLGSKGQLLRDLQLKPIDKESSSAIGYKPKDTAPSKAVLASLIRSSRVDQSHKHN 480
PDV P protein          421 KDGGLILGSKGQLLKDLQLKPIDKNSSSAIGFKPKDSAPSKAVIASLIRSSKVDQSHKQN 480
Rinderpest P protein   421 DTGKLGIESKGLLKKEFQLKPIEKKSSSAIRFVPDGSVASRSVIRSIIKSSHLGEDRKDY 480

AIK-C P protein        481 LMTLLDDIKGANDLAKFHQMLMKIIMK                                  507
Edmonston P protein    481 LMTLLDDIKGANDLAKFHQMLMKIIMK                                  507
CDV P protein          481 MLALLKNIKGDDNLNEFYQMVKSITHA                                  507
PDV P protein          481 MLSLLKNIKGDDNLNEFYQMIKSISHI                                  507
Rinderpest P protein   481 LMSLLNDIQGSKDLAQFHQMLVKILKN                                  507
```

METHOD FOR PRODUCING TEMPERATURE-SENSITIVE MORBILLIVIRUS

TECHNICAL FIELD

The present invention relates to methods for regulating temperature-sensitivity by a site-specific mutation of the morbillivirus-derived P protein. The P protein of this invention is useful in the attenuation of the virus.

BACKGROUND ART

The genus Morbillivirus is one of the genera under the family Paramyxoviridae of the order Mononegavirales, including many pathogenic viruses such as the measles virus that causes "measles"—an acute eruptive disorder. The measles virus widely infects infants, expressing symptoms such as fever, eruptions, cough, and such, occasionally causing severe complications such as measles-associated encephalitis, pneumonia, and such, sometimes even death. Furthermore, though very rarely, the measles virus sustains its infection even after the cure of infectious symptoms, causing encephalitis with a poor prognosis, named subacute sclerosing panencephalitis (SSPE). The one and only effective prophylactic means is vaccination with an attenuated measles virus vaccine.

The AIK-C strain, one of the attenuated measles virus vaccines, is a viral strain obtained by continual passage of the measles virus Edmonston strain in sheep kidney cells and chicken embryos cells. The AIK-C strain is excellent in its seroconversion rate as well as safety, which has earned it a high reputation internationally. With the spread of this attenuated measles vaccine, patients who contract measles have noticeably declined in number. In general, the seroconversion rate and safety of a vaccine are two incompatible characteristics, making it difficult to maintain both at a high standard. Therefore, if the mechanism of attenuation used in the AIK-C strain can be applied to other strains and viruses, it will be useful in the development of attenuated vaccines.

The AIK-C strain is known of its temperature-sensitivity (ts) to proliferate well at 32° C. but very poorly at 39° C. (Sasaki, K., Studies on the modification of the live AIK measles vaccine. I. Adaptation of the further attenuated AIK measles virus (the strain AIK-L33) to chick embryo cells. Kitasato Arch. of Exp. Med., 47, 1–12, 1974). However, the mechanism by which this virus strain becomes temperature-sensitive remains unclear.

DISCLOSURE OF THE INVENTION

An objective of the present invention is to provide DNA to be used for introducing a temperature-sensitivity character. Another objective of this invention is to provide methods for introducing a temperature-sensitivity character to a virus by a site-specific mutation of its P protein, and also to provide a virus having a temperature-sensitivity character due to a site-specific mutation in its P protein. Viruses having an introduced temperature-sensitivity character that are produced by the methods of this invention are useful in producing vaccines, and such as attenuated viruses.

The present inventors thought that, if a certain mutation in a viral protein is controlling a temperature-sensitivity, it may be possible to regulate viral proliferation and pathogenicity by identifying that mutation and producing a virus having such a mutant protein. Therefore, the present inventors searched for a gene involved in the temperature-sensitivity of the genus Morbillivirus using the N, P, and L genes derived from the AIK-C strain, which is a temperature-sensitive measles virus vaccine strain, and its parent non-temperature-sensitive Edmonston strain. As a result, the inventors discovered that the P gene is associated with the temperature-sensitivity.

Then the inventors introduced amino acid substitutions into the P gene of the Edmonston strain or AIK-C strain and examined effects of these mutant P genes on the temperature-sensitivity. As a result, the inventors found out that amino acid at the $439^{th}$ position of the P protein is closely associated with the temperature-sensitivity. In the Edmonston stain capable of proliferating at a high temperature, amino acid at the $439^{th}$ position of the P protein is leucine. Among P proteins having mutations at multiple positions, those having leucine at the $439^{th}$ position thereof as Edmonston strain has exhibit a viral proliferation ability equal to the P protein of the Edmonston strain. The inventors succeeded in introducing a temperature-sensitivity character by the mutation of this amino acid. Thus, this invention is the first to disclose a relationship between the $439^{th}$ amino acid in the P protein and temperature-sensitivity.

Based on the above-described knowledge, the present inventors discovered that modification of an amino acid at the $439^{th}$ position in the viral P protein enables the introduction of temperature-sensitivity character into viruses. Viruses having a temperature-sensitivity character introduced become difficult to proliferate and propagate in hosts, which leads to viral attenuation. Isolation of attenuated viruses useful in the development of vaccines has hitherto relied on screening for mutant viral strains, which is a low-efficient and time-consuming procedure. The present invention makes it possible to easily attenuate any desired viruses.

Furthermore, the present inventors discovered that, in addition to the $439^{th}$ amino acid in the P protein, amino acids at the $110^{th}$ and $275^{th}$ positions are also associated with the temperature-sensitivity. Therefore, modification of these amino acids also enables the introduction of temperature-sensitivity character.

Namely, the present invention relates to DNA used in introducing temperature-sensitivity character, methods for introducing temperature-sensitivity character into viruses by a mutation of a specific amino acid in the viral P protein, and a virus having a temperature-sensitivity character introduced due to a mutation at a specific position in the P protein, and more specifically relates to each of the following inventions:

[1] a DNA that encodes a protein derived from the P protein of a virus belonging to the genus Morbillivirus, wherein the protein encoded by the DNA comprises an amino acid other than leucine at a position corresponding to the $439^{th}$ position of a protein comprising the amino acid sequence set forth in SEQ ID NO: 2, and that is used for introducing a temperature-sensitivity character into a virus;

[2] a DNA that encodes a protein having at least 40% identity to the amino acid sequence set forth in SEQ ID NO: 2, wherein the protein encoded by the DNA comprises an amino acid other than leucine at a position corresponding to the $439^{th}$ position of a protein comprising the amino acid sequence set forth in SEQ ID NO: 2, and that is used for introducing a temperature-sensitivity character into a virus;

[3] the DNA according to [1] or [2], wherein the amino acid other than leucine is proline;

[4] the DNA according to any one of [1] through [3], wherein the DNA encodes a protein derived from a measles virus;

[5] the DNA according to [4], wherein the DNA further encodes a protein as described in the following (a) and/or (b):
 (a) a protein that comprises an amino acid other than aspartic acid at a position corresponding to the 110$^{th}$ position of a protein comprising the amino acid sequence set forth in SEQ ID NO: 2, and
 (b) a protein that comprises an amino acid other than cysteine at a position corresponding to the 275$^{th}$ position of a protein comprising the amino acid sequence set forth in SEQ ID NO: 2;

[6] the DNA according to [5], wherein the amino acid other than aspartic acid and/or the amino acid other than cysteine is tyrosine;

[7] the protein encoded by the DNA according to any one of [1] through [6];

[8] a vector into which the DNA according to any one of [1] through [6] is inserted;

[9] the vector according to [8], wherein the vector is used for reconstituting a measles virus into which a temperature-sensitivity character is introduced;

[10] a method for introducing a temperature-sensitivity character into a virus belonging to the genus Morbillivirus, said method comprising introducing a mutation into the P protein of the virus at an amino acid at a position corresponding to 439$^{th}$ position of a protein comprising the amino acid sequence set forth in SEQ ID NO: 2;

[11] a method for introducing a temperature-sensitivity character into a virus comprising a protein having at least 40% identity to the amino acid sequence set forth in SEQ ID NO: 2, said method comprising introducing a mutation into the protein at an amino acid at a position corresponding to the 439$^{th}$ position of a protein comprising the amino acid sequence set forth in SEQ ID NO: 2;

[12] the method according to [10] or [11], wherein the amino acid at a position corresponding to the 439$^{th}$ position is substituted with proline;

[13] the method according to any one of [10] through [12], wherein the virus is a measles virus;

[14] the method according to [13], wherein a mutation is further introduced into the protein at a amino acid described in the following (a) and/or (b):
 (a) an amino acid at a position corresponding to the 110$^{th}$ position of the protein comprising the amino acid sequence set forth in SEQ ID NO: 2, and
 (b) an amino acid at a position corresponding to the 275$^{th}$ position of the protein comprising the amino acid sequence set forth in SEQ ID NO: 2;

[15] the method according to [14], wherein the amino acid at a position corresponding to the 110$^{th}$ position and/or the amino acid at a position corresponding to the 275$^{th}$ position is substituted with tyrosine;

[16] a virus into which a temperature-sensitivity character is introduced, said virus being obtainable by the method according to any one of [10] through [15];

[17] the virus according to [16], wherein the virus is an attenuated virus;

[18] a pharmaceutical composition comprising the virus according to [16] or [17]; and

[19] the pharmaceutical composition according to [18], wherein the pharmaceutical composition is used as a vaccine.

The present invention also relates to the use of DNA in a method for producing a virus having a temperature-sensitivity character introduced, in which the DNA encodes a protein derived from the P protein of a virus belonging to the genus Morbillivirus wherein the protein encoded by the DNA comprises an amino acid other than leucine at a position corresponding to the 439$^{th}$ position of a protein comprising the amino acid sequence set forth in SEQ ID NO: 2. This invention also relates to the use of the DNA in producing a virus with a temperature-sensitivity character introduced, in which the DNA encodes a protein having at least 40% identity to the amino acid sequence set forth in SEQ ID NO: 2 and has an amino acid other than leucine at a position corresponding to the 439$^{th}$ position of a protein comprising the amino acid sequence set forth in SEQ ID NO: 2. Furthermore, the present invention relates to the use of a vector having such DNA in reconstituting a measles virus with a temperature-sensitivity character introduced.

The present invention relates to DNA used for introducing the temperature-sensitivity character. The DNA of this invention include DNA encoding a protein derived from the P protein of virus belonging to the genus Morbillivirus and having an amino acid other than leucine at a position corresponding to the 439$^{th}$ position in the P protein of the measles virus Edmonston strain (SEQ ID NO: 2). The DNA of this invention also include DNA encoding a protein having at least 40% identity to the amino acid sequence of the P protein in the Edmonston strain (SEQ ID NO: 2) and having an amino acid other than leucine at a position corresponding to the 439$^{th}$ position in the P protein of the Edmonston strain. Identity to the amino acid sequence set forth in SEQ ID NO: 2 is preferably 60% or more, more preferably 80% or more. Amino acid sequence identity can be determined by the 3 Lipman-Person method using Genetyx-Mac Ver. 10 (Software Development).

Examples of viruses belonging to the genus Morbillivirus are the measles virus, canine distemper virus, phocid distemper virus, rinderpest virus, etc.

In this invention, a protein comprising an amino acid sequence having at least 40% identity to the amino acid sequence set forth in SEQ ID NO: 2 has a structure similar to that of a protein comprising the amino acid sequence described in SEQ ID NO: 2. Therefore, it can be assumed that leucine at a position homologous to the 439$^{th}$ position in SEQ ID NO: 2, crucially influences the phenotype of temperature-sensitivity similar to the leucine at the 439$^{th}$ position in SEQ ID NO: 2. Furthermore, since viruses belonging to the genus Morbillivirus are taxonomically closely related to one another, the structure of the P proteins has been conserved among them. Therefore, leucine at a position homologous to the 439$^{th}$ position in SEQ ID NO: 2 can be assumed to crucially influence the phenotype of temperature-sensitivity. Results of comparisons of amino acid sequences in the P proteins of viruses belonging to the genus Morbillivirus are shown in FIG. 8. Thus, an amino acid corresponding to the 439$^{th}$ position in an amino acid sequence composing the P protein of each virus can be identified.

In this invention, whether a temperature-sensitivity character is introduced or not can be judged, for example, by a significantly poor growth shown by a virus having a target protein (in which amino acid at a position corresponding to the 439$^{th}$ position in the P protein is other than leucine) at a temperature at which a virus comprising a control protein having leucine at a position corresponding to the 439$^{th}$ position is able to grow, and, by a growth equivalent to that of the virus having the control protein shown by the virus of interest at a lower different temperature than that. Alternatively, when the optimum growth temperature for a virus comprising the target protein is significantly lowered compared to a virus having the control protein, that virus is judged to be temperature-sensitive. More specifically, for example, a virus that shows a poorer growth than the virus comprising the control protein at the body temperature of a host is judged to be temperature-sensitive.

In addition, "introduction of temperature-sensitivity" in this invention also includes an additional introduction of temperature sensitivity. That is, a virus whose original temperature-sensitivity is further elevated is also included in the virus having a temperature-sensitivity character introduced in the present invention. For example, in a virus having amino acid other than leucine at a position corresponding to the 439$^{th}$ position in the P protein and the control virus having leucine at that position, when the growth of a virus having amino acid other than leucine at a position corresponding to the 439$^{th}$ position in the P protein is significantly reduced compared to the control virus at a different temperature higher than the predetermined growth temperature, that virus can be said to be introduced with a temperature-sensitivity. This can be also judged based on the significantly lowered optimal growth temperature of virus.

Viral growth can be measured by calculating the virus amount in virus-infected cells or the culture supernatant thereof with time. For calculating the amount of virus such as the measles virus that brings about cytopathic effects (CPE) including cell degeneration and necrosis on appropriate sensitive cells, the plaque method and TCID50 method are mainly employed. In the plaque method, a single layer of cultured cells is prepared in a 35-mm Petri dish or 6-well culture plate, inoculated with 10-fold stepwise dilutions of virus sample, overlaid with agar, cultured, and then vital-stained with neutral red. Vital cells are stained red, while cells degenerated and necrotized due to viral infection are left unstained and observed as white spots (plaques). Plaque numbers in dishes expressing several tens to hundreds of plaques are counted to calculate the virus amount (PFU: plaque forming unit/ml) in the original sample solution. In the TCID50 method, a single layer of cells are prepared in a 96-well culture plate or the like. Ten-fold stepwise dilutions of viral solution are prepared, inoculated onto cells in 4 to 6 wells each for each dilution, and cultured for several days to confirm the CPE appearance. For the calculation of virus amount (TCID50 value), the Reed and Muench method can be employed (Reed, L. and Muench, H., A simple method of estimating fifty percent endpoints, Am. J. Hyg., 27, 493 (1938)).

Decrease in the viral growth potency due to the introduction of temperature-sensitivity character results in the achievement of attenuation of virus. On the other hand, based on the present invention, since the viral attenuation is achieved by mutation of merely a single amino acid, the structure as an antigen is maintained. Therefore, attenuation is effectively achieved with the seroconversion rate maintained at a high level.

The amino acid sequence of the P protein in the measles virus Edmonston strain and cDNA sequence encoding the protein are set forth in SEQ ID NOs: 2 and 1, respectively. In a protein of interest, a position homologous to the 439$^{th}$ position in the P protein of the Edmonston strain can be determined by comparing the amino acid sequences. The position in a protein of interest need not be the 439$^{th}$ position. For example, in the case of a protein having the structure of the P protein in the Edmonston strain that has been modified by, for example, an addition, insertion, and/or deletion of one or more amino acids, the homologous position may be a position other than the 439$^{th}$ position. In such a protein, to determine a position homologous to the 439$^{th}$ position in the P protein of the Edmonston strain, amino acid sequences of both proteins are aligned so as to match mutual amino acids as well as amino acids having similar properties as much as possible by inserting appropriate gaps in both amino acid sequences if necessary. Thus, it can be determined which position in a protein of interest corresponds to a position homologous to the 439$^{th}$ position in the P protein of the Edmonston strain. Such a technique has been known among those skilled in the art, and can be performed easily using commercially available or published computer software, for example, the analytical software GENETYX-MAC VER. 10 (Software), etc.

DNA encoding a protein of interest comprising an amino acid other than leucine at a position corresponding to the 439$^{th}$ position in the P protein of the Edmonston strain is used for introducing the temperature-sensitivity character according to this invention. There is no particular limitation on the origin of these DNA, which may be naturally occurring DNA or DNA into which a mutation has been artificially or spontaneously introduced. Alternatively, they may be DNA comprising artificially designed sequences.

The DNA of the present invention can be prepared using, for example, hybridization techniques well-known in the field (Sambrook, J., Fritsch, E. F., and Maniatis, T. Molecular Cloning: A Laboratory Manual (2$^{nd}$ edition). Cold Spring Harbor Laboratory Press, Cold Spring Harbor). DNA can also be isolated using the polymerase chain reaction technique (Sambrook, J., Fritsch, E. F., and Maniatis, T. Molecular Cloning: A Laboratory Manual (2$^{nd}$ edition). Cold Spring Harbor Laboratory Press, Cold Spring Harbor).

That is, those skilled in the art can isolate DNA by screening virus-derived DNA, and such, using the hybridization technique and PCR method. Nucleotide sequences of probes necessary in the hybridization method and primers required in the PCR method can be designed based on, for example, the cDNA sequence (SEQ ID NO: 1) of the P protein of the Edmonston strain. By identifying the position in the amino acid sequence encoded by the isolated DNA, which is homologous to the 439$^{th}$ position in the P protein of the Edmonston strain, DNA encoding a protein having an amino acid other than leucine at that position can be readily prepared.

By appropriately modifying the DNA thus obtained, the amino acid in the protein encoded by the DNA, which is at a position corresponding to the 439$^{th}$ position in the P protein of the Edmonston strain, can be substituted with any desired amino acid other than leucine. Alternatively, the introduction of a mutation so as to delete the leucine is also included in this invention. The amino acid used for the substitution, can be appropriately selected. As described in Examples, a protein having an amino acid that was substituted with proline at a position homologous to the 439$^{th}$ position in the P protein of the Edmonston strain gave the temperature-sensitivity character to viruses. Therefore, DNA encoding a protein having an amino acid that was modified with proline at a position homologous to the 439$^{th}$ position in the P protein of the Edmonston strain can be preferably used in the present invention.

Furthermore, the present invention proved that an amino acid at this position in the P protein crucially influences the phenotype of temperature-sensitivity. Therefore, in the case where an amino acid other than leucine is present at the corresponding position, the temperature-sensitivity may be further elevated or, reversely, the degree of the elevation of temperature-sensitivity may be lowered by further mutating this amino acid to another amino acid. The elevation of the temperature-sensitivity and introduction of temperature-sensitivity character in the present invention include cases where the function of P protein is completely inactivated in the whole temperature range.

Methods for introducing a mutation into an amino acid in a protein are well known. For example, DNA encoding a desired amino acid sequence can be isolated by preparing a viral library comprising mutant viruses, DNA library encoding mutant P proteins, and such, and screening them for the desired DNA. Alternatively, mutant viruses can be screened from nature. Furthermore, site-specific mutagenesis can be performed using well-known genetic engineering techniques. For the introduction of site-specific mutations, for example, the SOE (splicing-by-overlap-extension)-PCR method (Ho, S. N., Hunt, H. D., Horton, R. M., Pullen, J. K., and Pease, L. R. (1989) Gene 77, 51–59), and Kunkel method (Kunkel, T. A. (1985) Proc. Natl. Acad. Sci. U.S.A. 82 (2): 488–92) can be used.

In addition, in the present invention, as long as the amino acid at a position corresponding to the $439^{th}$ position in the P protein is any amino acid other than leucine, a position other than that may be further modified. As shown in Examples, for example, it was revealed that, in the P protein (SEQ ID NO: 2) of the Edmonston stain, the temperature-sensitivity is elevated by substituting aspartic acid at the $110^{th}$ position with tyrosine (FIGS. 5 and 6; pCIP005). Also, for example, when cysteine at the $275^{th}$ position is substituted with tyrosine, the temperature-sensitivity was elevated (FIGS. 5 and 6; pCIP003). These facts indicate that mutation of amino acids at the $110^{th}$ and $275^{th}$ positions results in the elevation of viral temperature-sensitivity. Therefore, DNA encoding proteins whose amino acid at a position corresponding to the $439^{th}$ position of the P protein is amino acid other than leucine, and whose amino acids at positions corresponding to the $110^{th}$ and/or $275^{th}$ positions are those other than aspartic acid and/or cysteine, respectively, are preferable for more effectively introducing the temperature-sensitivity character. Preferably, amino acids at positions corresponding to the $110^{th}$ and/or $275^{th}$ positions can be tyrosine. In a naturally-occurring virus, when amino acid at positions corresponding to the $110^{th}$ and/or $275^{th}$ positions is tyrosine, this can be used for introducing temperature-sensitivity according to this invention, leaving amino acid at these positions untouched. Also, by mutating amino acids at these positions to, for example, aspartic acid, the degree of temperature-sensitivity may be attenuated.

In addition, the DNA of this invention include DNA encoding proteins having an amino acid other than leucine at the $439^{th}$ position of the P protein in the Edmonston strain (SEQ ID NO: 2) and also having one or more substitution, deletion, insertion, and/or addition of amino acids other than that at the $439^{th}$ position. In the case of the artificial modification of amino acids in the P protein encoded by DNA obtained from viruses belonging to Morbillivirus, the number of amino acids modified is usually ten or less, preferably five or less, even more preferably, three amino acid excluding the one at the position corresponding to the $439^{th}$ position. Such an amino acid modification can be performed, for example, aiming at further elevating the temperature-sensitivity of the P protein, and also aiming at improving the manipulability of DNA, for example, by the insertion of a restriction enzyme site, and such, and also with the aim of modifying a property of the P protein other than its temperature-sensitivity. Mutations of amino acids in proteins may occur also in nature.

In general, to minimize the loss of properties of a protein as much as possible, an amino acid used for substitution is thought to be preferably one with a property similar to the substituted amino acid. For example, Ala, Val, Leu, Ile, Pro, Met, Phe, and Trp are all classified into the non-polar amino acid group, and thought to have similar properties. Furthermore, non-charged amino acids are exemplified by Gly, Ser, Thr, Cys, Tyr, Asn, and Gln. Acidic amino acids are exemplified by Asp and Glu, and basic amino acids by Lys, Arg, and His.

Furthermore, the present invention relates to proteins encoded by the DNA of this invention. The temperature-sensitivity character can be introduced into viruses using the proteins of this invention. A protein of this invention can be expressed by inserting DNA encoding the protein into an appropriate expression vector, and introducing the vector into host cells. In the measles virus, and such, viruses with a temperature-sensitivity character introduced can be reconstituted from vectors having DNA encoding the proteins of this invention. Several methods for reconstituting the measles virus from cDNA have been reported, namely, the method of Radecke (Radecke, F., Spielhofer, P., Schneider, H., Kaelin, K., Huber, M., Dotsch, C., Christiansen, G. and Billeter, M. A. (1995) EMBO J. 14(23): 5773–84) and the method of Schneider (Schneider, H., Spielhofer, P., Kaelin, K., Dotsch, C., Radecke, F., Sutter, G. and Billeter, M. A. (1997) J. Virol. Methods 64(1): 57–64). According to these methods, a measles virus can be reconstituted from DNA encoding the N, P, M, F, H, and L proteins of the measles virus. Therefore, by using the DNA of this invention as DNA encoding this P protein, a measles virus with a temperature-sensitivity character introduced can be reconstituted. That is, transcription of DNA encoding the N, P, M, F, H, and L proteins allows their transcription products to function as genomic RNA of the measles virus, so that measles viral particles can be formed in the presence of the N, P, and L proteins. The virus thus obtained can be further amplified by infecting the virus to appropriate hosts.

Several methods for reconstituting morbilliviruses other than the measles virus are known. For example, the method of Baron, et al. (Baron, M. D., and Barrett, T. (1997) J. Virol. 71(2): 1265–71); the method of Kai, et al. (Kai, C., Miura, R., Shimizu, F., Sato, H., Fujita, K., Hatama, S., Ohashi, K., Kamima, T., and Takahashi, E. Abstracts of the $47^{th}$ General Assembly of the Japanese Society for Virology (1999), p. 289: Preparation of recombinant canine distemper virus using the reverse genetic method), and furthermore, Patent WO97/16538 are known.

In addition to the present invention, it is possible to reduce cell-fusion ability in a virus by mutating the viral F protein together with the introduction of temperature-sensitivity character. The present inventors have proved that a cell-fusion ability can be reduced in morbilliviruses using a protein having an amino acid other than phenylalanine at a position corresponding to the $278^{th}$ position of the F protein of the measles virus Edmonston strain. Combination of this knowledge with the instant invention enables one to alter the cell-fusion ability together with the temperature-sensitivity, providing extremely safer vaccine preparations.

It is also possible to provide a safe and excellent vaccine preparation with a different antigenicity by incorporating DNA encoding the measles viral protein with a different antigenicity, for example, a gene expressing the H protein that is most closely associated with phylaxis into a vector comprising DNA encoding a protein whose amino acid at the 439$^{th}$ position of P protein or its homologous position is other than leucine, and a protein whose amino acid at the 278$^{th}$ position of F protein or its homologous position is other than phenylalanine, and transfecting the resulting recombinant vector into host cells to reconstitute a virus.

In addition, the present invention relates to methods for introducing a temperature-sensitivity character into virus. A method of this invention is characteristic in that, in a protein having at least 40% identity with the amino acid sequence of the P protein of virus belonging to the genus Mobillivirus or Edmonston strain, a mutation is introduced to amino acid at the 439$^{th}$ position of P protein (SEQ ID NO: 2) of the measles virus Edmonston strain or its homologous position. Although there is no particular limitation on the type of mutation to be introduced, substitution with proline is one example. The temperature-sensitivities of viruses that can be obtained by this invention can be compared by the above-described methods.

In the above-described protein, it is further possible to introduce mutation to amino acids at positions corresponding to the 110$^{th}$ and/or 275$^{th}$ positions in the P protein (SEQ ID NO: 2) of the measles virus Edmonston stain, and further additionally confer the viral temperature-sensitivity character. Amino acids at these positions can be substituted, for example, with tyrosine.

Viruses thus obtained having a temperature-sensitivity character introduced are less pathogenic because their proliferation and propagation abilities in hosts are reduced. These viruses are extremely useful for producing safe live vaccines. According to the present invention, any virus strain can be attenuated by modifying its P protein using genetic engineering technology. When a virus of this invention is used as a pharmaceutical composition such as a vaccine, besides the use of the virus itself as a drug, it can be formulated by applying a known pharmaceutical procedure. For example, the virus may be administered as a pharmaceutical preparation by appropriately combining with a pharmacologically acceptable carrier or media, more specifically, sterilized water, physiological saline, a plant oil, emulsifier, suspending agent, surfactant, stabilizer, etc. When using the virus as a vaccine, it can be administered suitably in combination with an adjuvant. Administration to patients can be performed by methods known to those skilled in the art, for example, besides the intra-arterial, intravenous, and subcutaneous injections, it can be given intranasally, transbronchially, intramuscularly, percutaneously, or orally. Doses may vary depending on the weight and age of patients as well as the method of administration, purpose of usage, and so on, and may be appropriately selected by one skilled in the art.

In general, in Japan, the vaccine strain of the measles virus is cultured by inoculation to cultured chicken embryos cells prepared from embryonated eggs produced in SPF facilities approved by the Japanese Ministry of Health and Welfare. After the culture, a stabilizer is added to a vaccine solution that has cleared the germ-free test, and purified to obtain an undiluted vaccine concentrate. This vaccine concentrate is stored at −80° C., and at the same time examined for its safety and efficacy. Vaccine concentrates that have cleared the test are pooled as the final bulk, from which vaccine preparations are made. Those that have cleared repeated national tests and private tests are sold as the final preparation.

Furthermore, the viruses of the present invention can be used as vectors for gene therapy.

All the prior art literatures cited herein are incorporated by reference.

BRIEF DESCRIPTION OF THE DRAWINGS

FIG. 8 represents the results of comparing amino acid sequences of P proteins of viruses belonging to the genus Mobillivirus. Positions homologous to the 439$^{th}$ position are enclosed in the box. Shown from the top are amino acid sequences of P proteins of the AIK-C strain, Edmonston strain, canine distemper virus, phocid distemper virus, and rinderpest virus.

BEST MODE FOR CARRYING OUT THE INVENTION

The present invention will be described in more detail below with reference to examples, but it is not to be construed as being limited thereto.

Example 1

Figure 1:
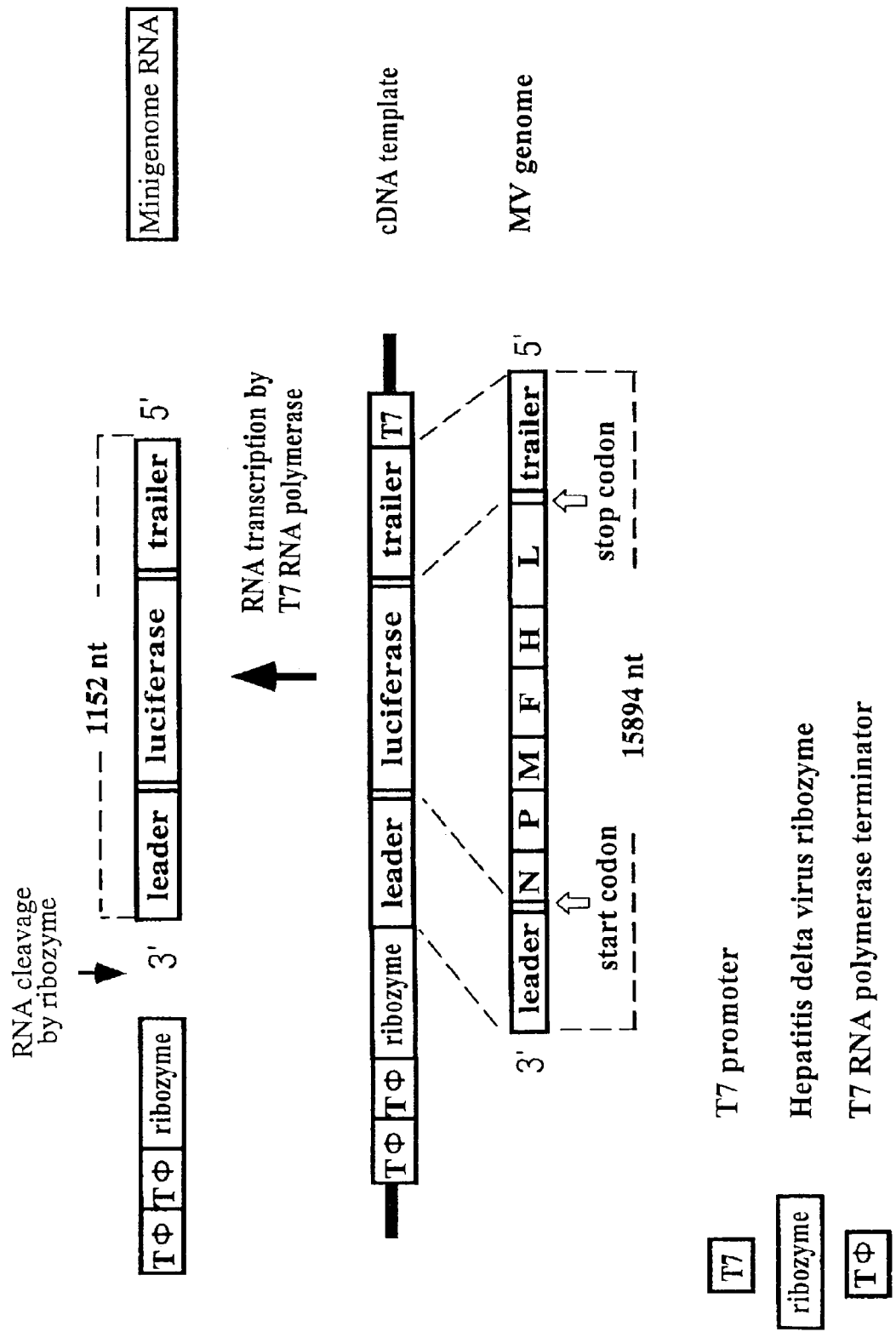
FIG. 1 represents the structure of the template cDNA used for synthesizing a minigenome RNA.

Identification of Gene Involved in Temperature-Sensitivity of Measles Virus ATK-C Strain Using cDNA derived from the measles virus Edmonston strain, a template DNA used for the minigenome RNA synthesis comprising the *Renilla reniformis* luciferase gene as a reporter gene was constructed. This DNA used for the minigenome RNA synthesis comprises the measles virus leader sequence, non-coding sequence upstream of the N gene, *Renilla reniformis* luciferase gene, non-coding sequence downstream of the L gene, and trailer sequence, and 1,152 nucleotides long. The T7 promoter sequence was set downstream of the trailer sequence, and ribozyme sequence was placed upstream of the leader sequence. These two sequences were arranged so that both ends of the minigenome RNA accurately would reproduce the both ends of measles virus genomic RNA when the minigenome RNA was synthesized by the in vitro transcription method using T7 RNA polymerase (FIG. 1).

N, P, and L genes derived from the measles virus Edmonston strain and AIK-C strain were cloned, and subcloned into the pCITE-4a plasmid (Novagen, USA) comprising the IRES structure downstream of the T7 promoter to form the pCIN01 (expressing the Edmonston N protein), pCTP001

(expressing the Edmonston P protein), pCIL01 (expressing the Edmonston L protein), pCIAN01 (expressing the AIK-C N protein) pCIAP001 (expressing the AIK-C P protein), and pCIAL01 (expressing the AIK-C L protein), respectively.

Figure 2:
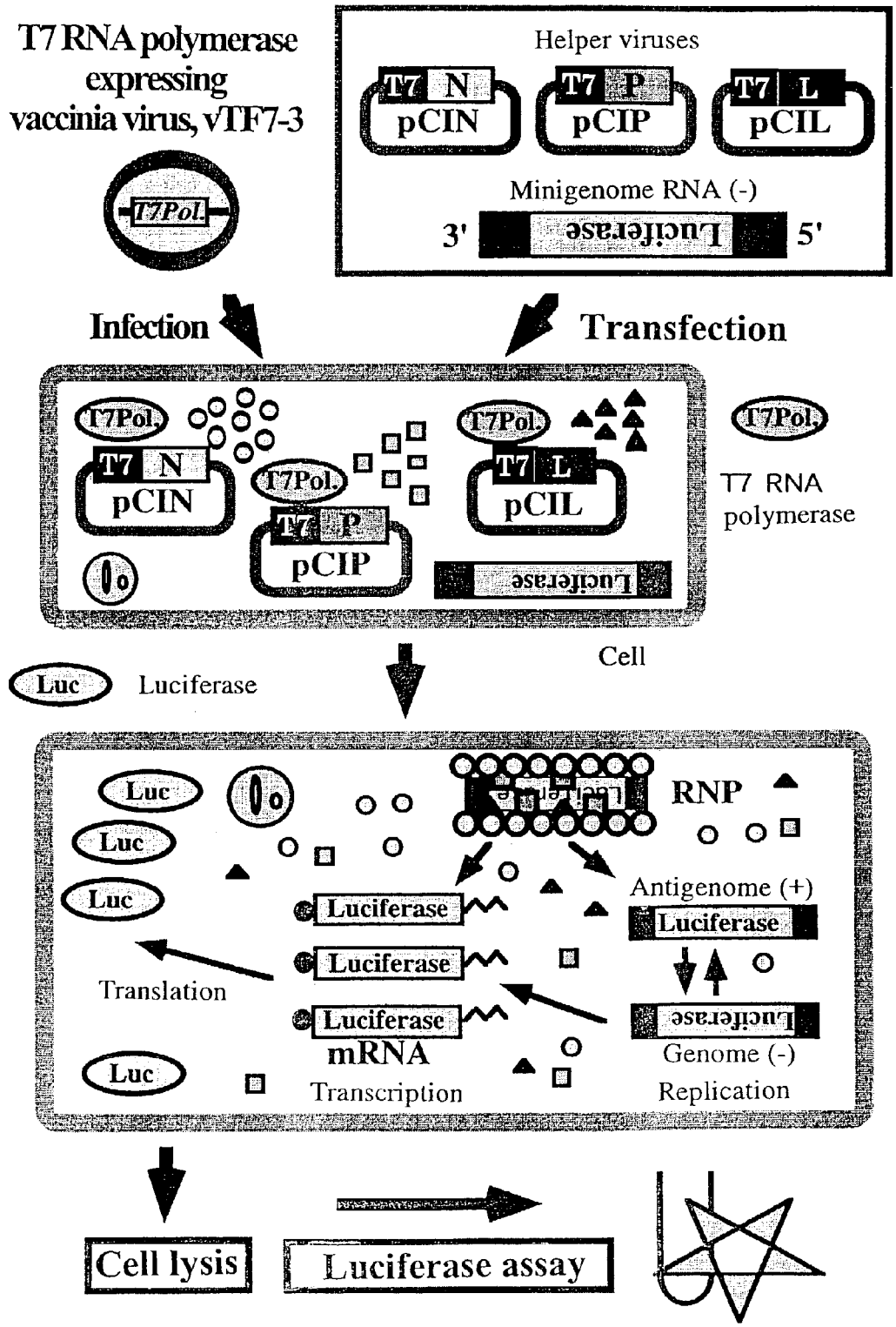
FIG. 2 represents the experimental procedures of a minigenome system using the vaccinia virus vTF7-3.

HeLa cells were prepared in 12-well plates, infected with the vaccinia virus vTF7-3 expressing T7 RNA polymerase at an m.o.i. of 3, and then co-transfected with the above-described helper plasmids expressing the measles virus N, P, and L proteins and the synthesized minigenome RNA. After a 40-hour incubation, cells were washed, and lysed to collect the cell extract. Luciferase activity in this cell extract was measured (FIG. 2).

Figure 3:
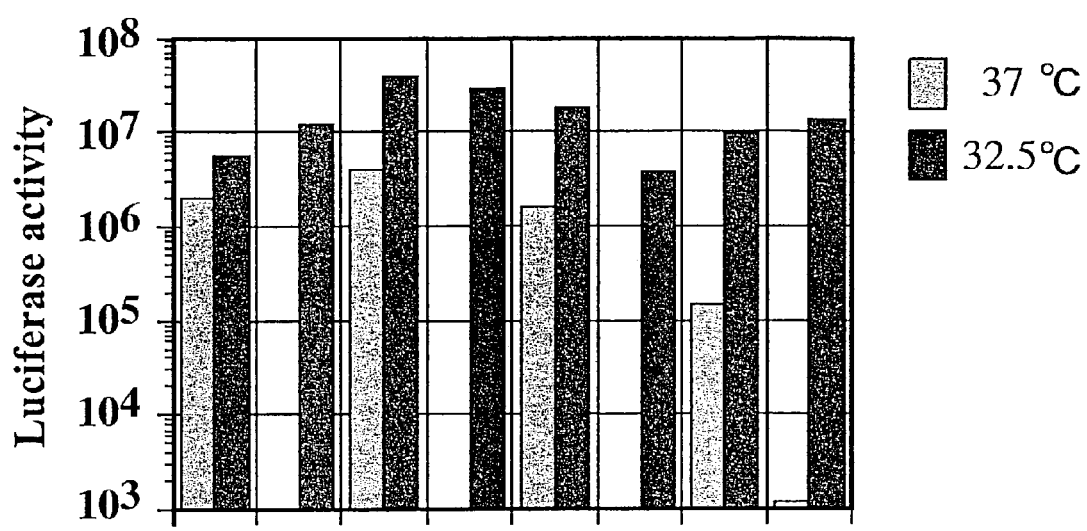
FIG. 3 represents the luciferase expression in a minigenome system using various combinations of plasmids expressing N, P, and L proteins derived from the Edmonston strain and AIK-C strain.

Using the minigenome transcription/replication system, the luciferase expression level was observed at 32.5° C. or 37° C. in combinations of expression plasmids for N, P, and L proteins derived from Edmonston strain and AIK-C strain. As a result, the luciferase expression was not observed in a system containing the P gene of AIK-C strain at 37° C., indicating the involvement of AIK-C P gene in the temperature-sensitivity (FIG. 3).

Example 2

Figure 4:
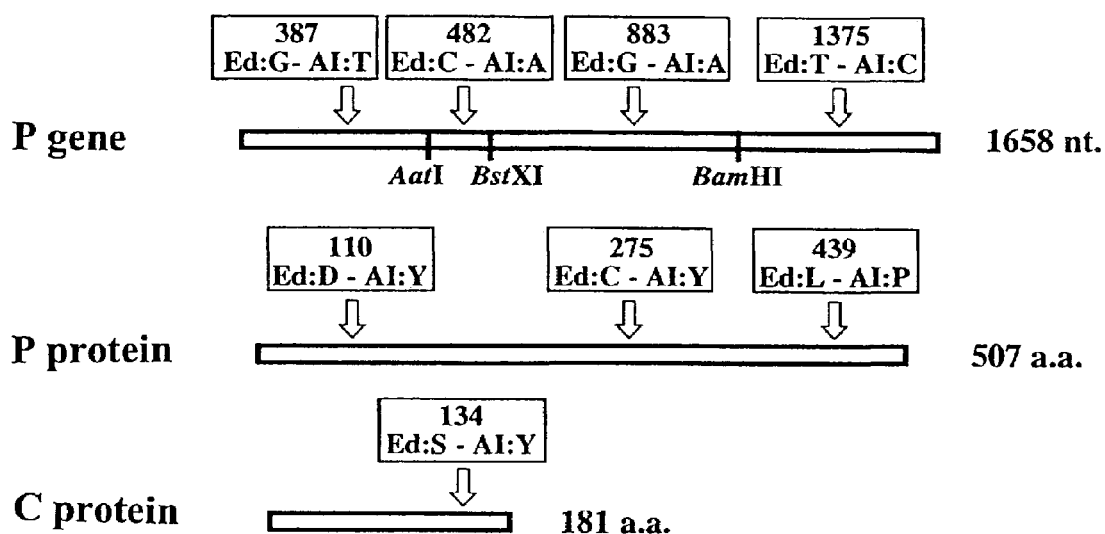
FIG. 4 represents amino acid mutations observed in P and C proteins derived from the AIK-C strain and Edmonston strain.

Identification of Amino Acid Mutation on P Protein Involved in Temperature-Sensitivity of AIK-C Strain Amino acid mutations observed on the P and C proteins derived from the AIK-C and Edmonston strains were inferred from their respective nucleotide sequences. Nucleotide sequence of cDNA encoding P and C proteins of Edmonston strain is set forth in SEQ ID NO: 1, and amino acid sequences of P and C proteins encoded by said cDNA are shown in SEQ ID NOs: 2 and 3, respectively. Nucleotide sequence of cDNA encoding P and C proteins of AIK-C strain is set forth in SEQ ID NO: 4, and amino acid sequences of P and C proteins encoded by said cDNA are shown in SEQ ID NOs: 5 and 6, respectively. On the P proteins were found differences in amino acids at the $110^{th}$ position (Edmonston; D, AIK; Y), $275^{th}$ position (Edmonston; C, AIK; Y), and $439^{th}$ position (Edmonston; L, AIK; P), while, on the C protein, another protein encoded by the P gene, was a difference in amino acid at the $134^{th}$ position (Edmonston; S, AIK; Y) (FIG. 4).

Figure 5:
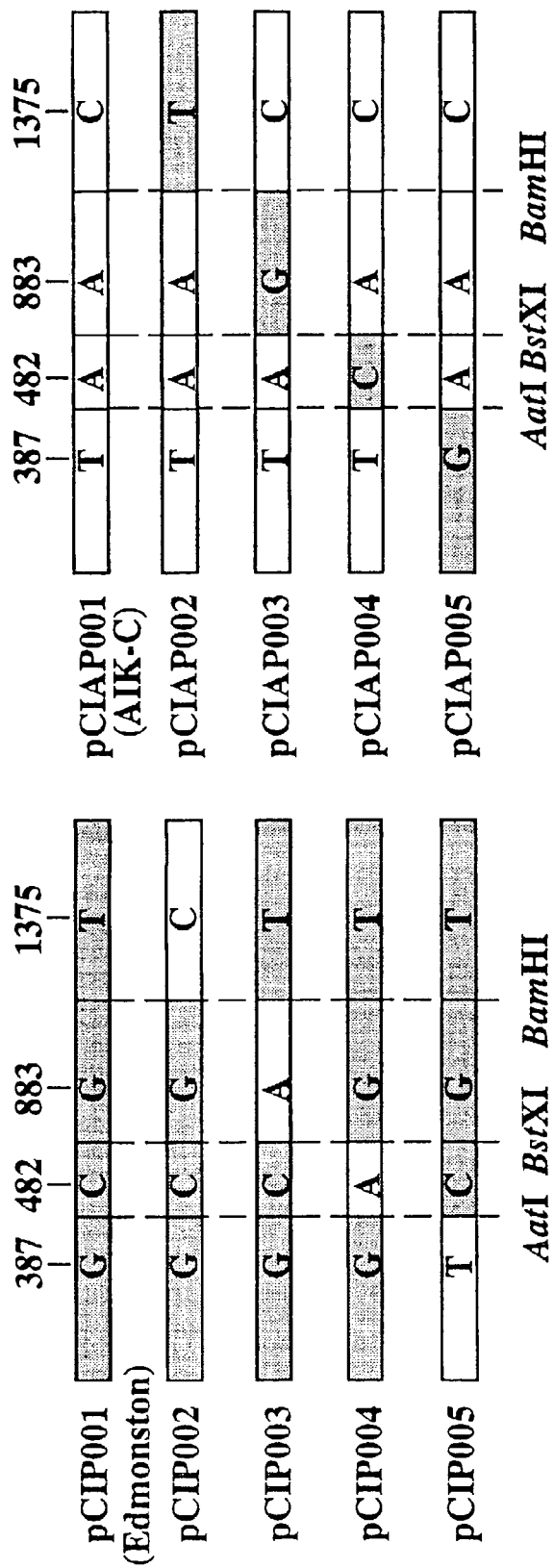
FIG. 5 represents structures of various P expression plasmids.

An amino acid at the mutation sites found in P proteins was replaced with a different amino acid to construct eight chimeric plasmids: pCIP002, pCIP003, pCIP004, pCIP005, pCIAP002, pCIAP003, pCIAP004, and pCIAP005 (FIG. 5).

Figure 6:
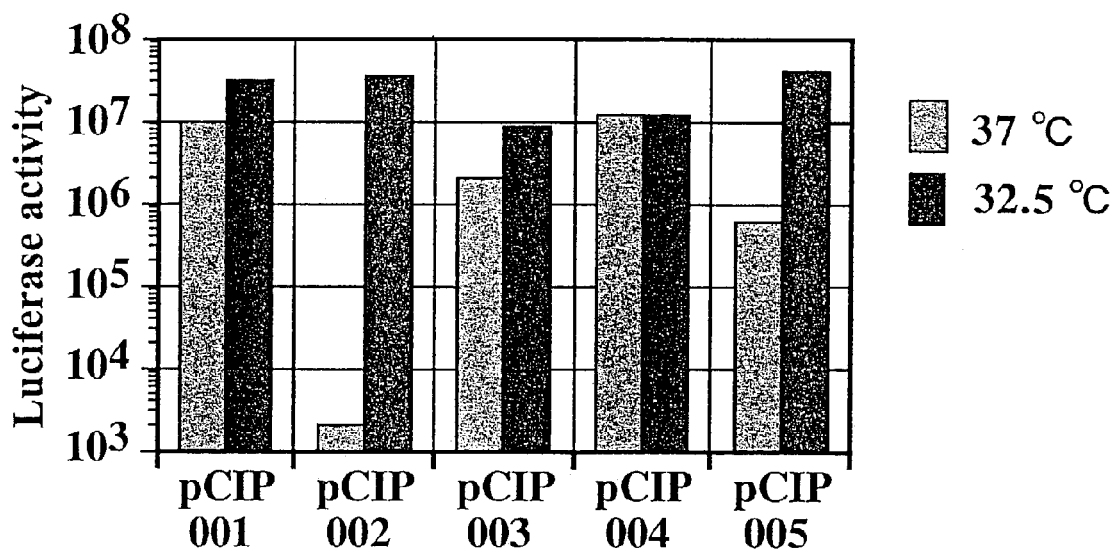
FIG. 6 represents the luciferase expression in a minigenome system using P expression plasmids shown in FIG. 5.
Figure 6:
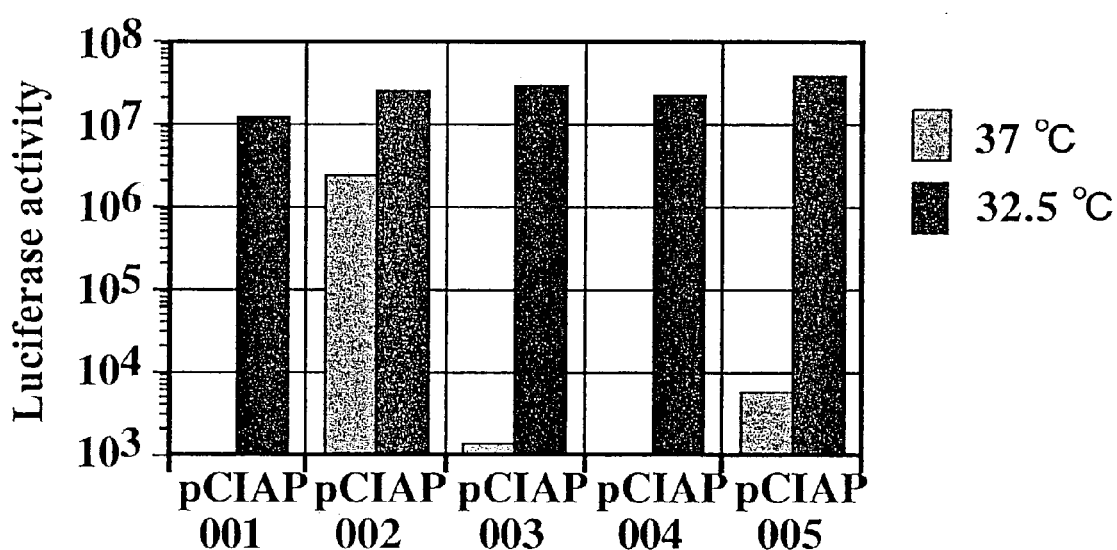

Using these chimeric plasmids, the minigenome transcription/replication system was similarly operated as described above together with the pCIN01 and pCIL01 plasmids. When pCIP002 was used, the luciferase expression was not observed at 37° C., while, on the contrary, it was seen at 37° C. when pCIAP002 was used. Thus, it was thought that amino acid at the $439^{th}$ position (proline (P)) on the AIK-C P protein is involved in the temperature-sensitivity (FIG. 6). Furthermore, the luciferase expression was slightly suppressed with pCIP005 at 37° C., and weak expression was observed with pCIAP005, so that amino acid at the $110^{th}$ position (tyrosine (Y)) was thought also to be associated with the temperature-sensitivity. In addition, with pCIP003, a slightly suppressed luciferase expression was observed at 37° C., and with pCIAP003, weak expression was seen, so that amino acid at the $275^{th}$ position (tyrosine (Y)) is assumed to be also involved in the temperature-sensitivity.

Example 3

Relationship Between Amino Acid Substitutions and Temperature-Sensitivity Examined Using Infectious Clones Using the reverse genetics, the following mutated recombinant measles viruses (infectious clones) were prepared on the basis of the whole cDNA of the AIK-C strain:

(i) a virus in which the P gene is that of AIK-C strain (AIK-P infectious clone), (ii) a virus in which only the P gene (P protein) is substituted with the Edmonston strain P gene (P protein) (Edm-P infectious clone), (iii) a virus in which only an amino acid at the $439^{th}$ position of the P gene (P protein) is substituted with leucine ($439^{th}$ amino acid of Edmonston P protein) and the other amino acids are the same as those of the AIK-C strain P protein (AIK/Edm-P infectious clone), and (iv) a virus in which only the amino acid at the $439^{th}$ position of the P protein in (ii) is substituted with proline ($439^{th}$ amino acid of AIK-C P protein) (Edm/AIK-P infectious clone).

Vero cells were infected with each virus at an m.o.i. of 0.05, and cultured at each temperature of 32.5° C., 37° C., and 39° C. to measure the time-course of the intracellular virus titer. Namely, to measure the intracellular virus level 24, 48, 72, and 96 hours later, virus-infected Vero cells were recovered together with the culture medium from plates at each predetermined time as above, centrifuged once to remove the culture supernatant, and resuspended in a fresh culture medium (0.5 ml). The cells were sonicated, and centrifuged again to recover the supernatant. B95a cells were cultured in 96-well plates, and 10-fold stepwise dilutions of the virus solution prepared from the recovered supernatant were inoculated at 0.25 μl to 4 wells each for one dilution. After culturing at 32.5° C. for 7 days, CPE expression was observed, and the amount of virus in 1 ml of the recovered virus original solution (TCID 50/ml) was calculated by the Reed and Muench method (Reed, L. and Muench, H., A simple method of estimating fifty percent endpoints. Am. J. Hyg., 27, 493 (1938)).

Figure 7:
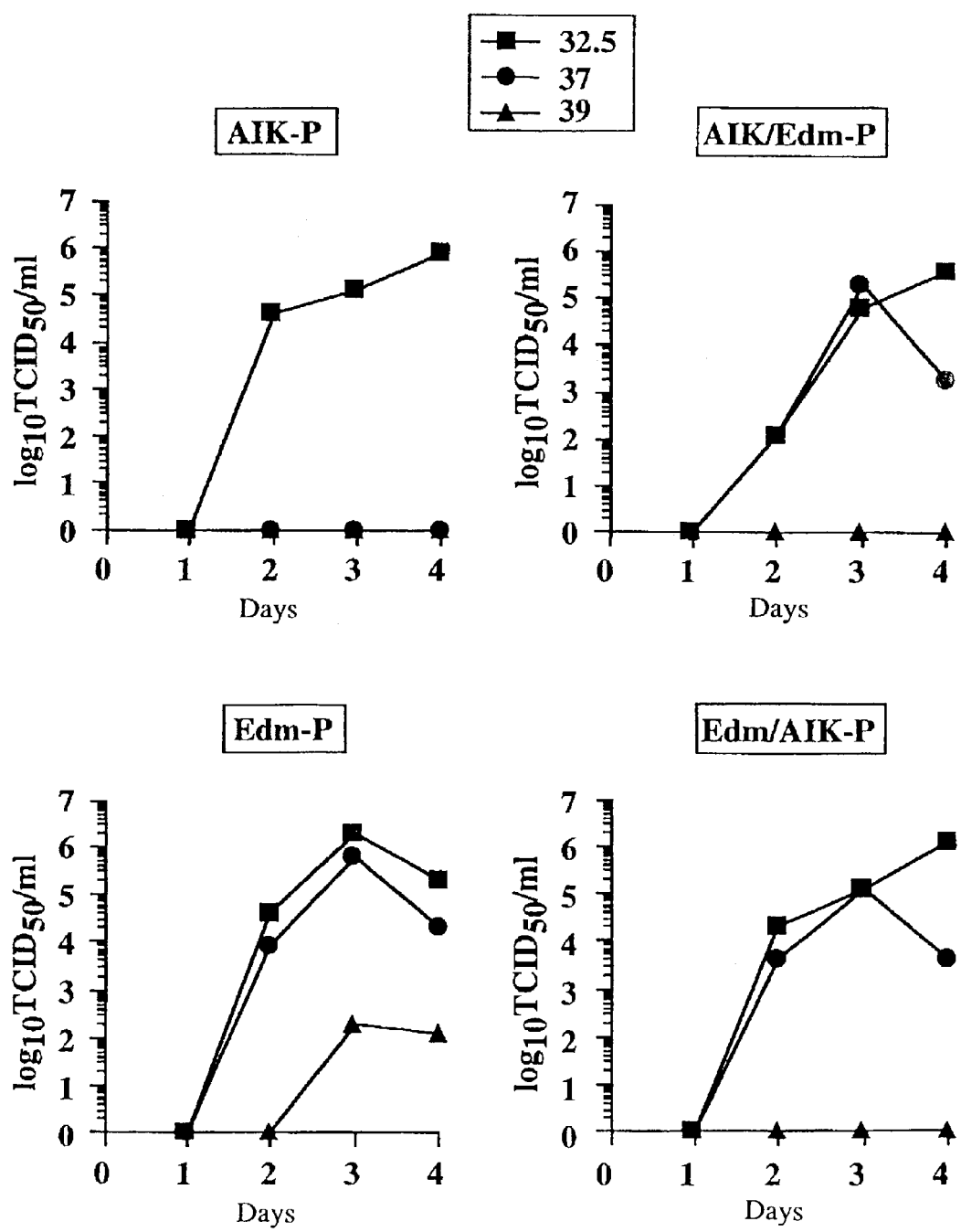
FIG. 7 represents the results of investigating the growth of reconstituted measles viruses having various P genes examined at respective temperatures.

As a result of experiments, at 32.5° C., when any one of the P genes was used, those infectious clone viruses were observed to grow to approximately the same level. In addition, at 37° C., AIK-P infectious clone virus (i) did not grow. In contrast to this, Edm/AIK-P infectious clone (iii), whose $439^{th}$ amino acid was substituted with leucine, grew even at 37° C. (FIG. 7).

From these results, it was revealed that the viral temperature-sensitivity character can be introduced by the mutagenesis of amino acid at the $439^{th}$ position (leucine). On the other hand, the Edm-P infectious clone (ii), in which the P gene was replaced with Edmonston-P, grew at 37° C. and weakly grew at 39° C. Furthermore, the AIK/Edm-P infectious clone, in which amino acid at the $439^{th}$ position (leucine) of Edm-P infectious clone was substituted with proline, could grow at 37° C. but not at 39° C., indicating that mutation at a position other than the $439^{th}$ position of the P protein may be involved in the temperature-sensitivity. It is inferred that, in addition to the $439^{th}$ amino acid of the P protein, amino acids: Ys at the $110^{th}$ and $275^{th}$ positions are possibly involved in the temperature-sensitivity. Furthermore, amino acid: Y at the 134th position of the C protein encoded also by the P gene is assumed to be involved in the temperature-sensitivity, too.

INDUSTRIAL APPLICABILITY

The present invention provides DNA used for producing a temperature-sensitive virus, methods for introducing the temperature-sensitivity character into viruses by a site-specific mutagenesis of the viral P protein, and viruses with a temperature-sensitivity character introduced by a site-specific mutation in the P protein. Thus, the instant invention enables the easy production of attenuated viruses, thereby enables the speedy development of live vaccines against novel newly emerging viruses.

Besides the measles virus, the genus Morbillivirus in particular includes many pathogenic viruses, such as the canine distemper virus, phocid distemper virus, and rinderpest virus. Therefore, the methods of the present invention capable of attenuating viruses of the genus Morbillivirus with a minimal mutation are highly useful in the development of vaccines.

The invention claimed is:

1. An isolated polynucleotide that encodes a Morbillivirus P protein, wherein said Morbillivirus is other than the AIK-C measles virus strain, wherein said P protein has a mutation of an amino acid at a position corresponding to the $439^{th}$ position of a protein comprising the amino acid sequence set forth in SEQ ID NO: 2, and wherein said mutation confers temperature-sensitivity on the virus when introduced into the virus.

2. The polynucleotide according to claim 1, wherein said polynucleotide encodes a protein having at least 40% identity to the amino acid sequence set forth in SEQ ID NO: 2, wherein the protein has a mutation of an amino acid at a position corresponding to the $439^{th}$ position of a protein comprising the amino acid sequence set forth in SEQ ID NO: 2, wherein said mutation confers temperature-sensitivity on the virus when introduced into the virus.

3. The polynucleotide according to claim 1, wherein the mutation of an amino acid is a substitution to proline.

4. The polynucleotide according to claim 1, wherein the polynucleotide encodes a measles virus P protein.

5. The polynucleotide according to claim 1, wherein the P protein has an additional mutation of an amino acid at a position corresponding to the $110^{th}$ and/or $275^{th}$ position of a protein comprising the amino acid sequence set forth in SEQ ID NO: 2, wherein said additional mutation confers temperature-sensitivity on the virus when introduced into the virus.

6. The polynucleotide according to claim 5, wherein either or both additional mutation(s) is a substitution to tyrosine.

7. An isolated or recombinantly expressed P protein of a Morbillivirus other than the AIK-C measles virus strain wherein said P protein comprises a mutation of an amino acid at a position corresponding to the $439^{th}$ position of a protein comprising the amino acid sequence set forth in SEQ ID NO: 2, and wherein said mutation confers temperature-sensitivity on the virus when introduced into the virus.

8. An expression vector into which the isolated polynucleotide according to claim 1 is inserted.

9. The vector according to claim 8, wherein the vector is used for reconstituting a measles virus on which temperature-sensitivity is conferred.

10. A method for conferring temperature-sensitivity on a Morbillivirus, said method comprising introducing, into a Morbillivirus P protein, a mutation of an amino acid at a position corresponding to $439^{th}$ position of a protein comprising the amino acid sequence set forth in SEQ ID NO: 2.

11. The method of claim 10, wherein the Morbillivirus P protein has at least 40% identity to the amino acid sequence set forth in SEQ ID NO: 2.

12. The method according to claim 10, wherein the mutation of an amino acid is a substitution to proline.

13. The method according to claim 10, wherein the Morbillivirus is a measles virus.

14. The method according to claim 10, wherein said method further comprises introducing, into the Morbillivirus P protein, an additional mutation of an amino acid at a position corresponding to the 110$^{th}$ and/or 275$^{th}$ position of a protein comprising the amino acid sequence set forth in SEQ ID NO: 2.

15. The method according to claim 14, wherein each of the mutations of an amino acid at a position corresponding to the 110$^{th}$ and/or 275$^{th}$ position is a substitution to tyrosine.

16. An isolated Morbillivirus on which temperature-sensitivity is conferred, wherein said virus comprises a polynucleotide according to claim 1.

17. The virus according to claim 16, wherein the virus is an attenuated virus.

18. A pharmaceutical composition comprising the virus according to claim 16 and a pharmacologically acceptable carrier or medium.

19. The pharmaceutical composition according to claim 18, wherein the pharmaceutical composition is used as a vaccine.

20. The virus according to claim 16, wherein said virus is obtainable by a method comprising introducing a mutation into the P protein of the virus at an amino acid at a position corresponding to the 439$^{th}$ position of a protein comprising the amino acid sequence set forth in SEQ ID NO: 2.

21. The Morbillivirus P protein according to claim 7, wherein said protein has at least 40% identity to the amino acid sequence set forth in SEQ ID NO: 2.

22. The Morbillivirus P protein according to claim 7, wherein the mutation of an amino acid is a substitution to proline.

23. The Morbillivirus P protein according to claim 7, wherein the protein is a measles virus P protein.

24. The Morbillivirus P protein according to claim 7, wherein the P protein further has an additional mutation of an amino acid at a position corresponding to the 110$^{th}$ and/or 275$^{th}$ position of a protein comprising the amino acid sequence set forth in SEQ ID NO: 2, wherein said additional mutation further confers temperature-sensitivity on the virus when introduced into the virus.

25. The Morbillivirus P protein according to claim 23, wherein either or both additional mutation(s) is a substitution to tyrosine.

26. A method for producing a Morbillivirus on which temperature-sensitivity is conferred, said method comprising introducing, into a Morbillivirus P protein, a mutation of an amino acid at a position corresponding to the 439$^{th}$ position of a protein comprising the amino acid sequence set forth in SEQ ID NO: 2.

27. The method according to claim 26, wherein the Morbillivirus P protein has at least 40% identity to the amino acid sequence set forth in SEQ ID NO: 2.

28. The method according to claim 26, wherein the mutation of an amino acid is a substitution to proline.

29. The method according to claim 26, wherein the virus is a measles virus.

30. The method according to claim 26, wherein said method further comprising introducing, into the Morbillivirus P protein, an additional mutation of an amino acid at a position corresponding to the 110$^{th}$ and/or 275$^{th}$ position of a protein comprising the amino acid sequence set forth in SEQ ID NO: 2.

31. The method according to claim 30, wherein either or both additional mutation(s) is a substitution to tyrosine.

32. The virus according to claim 16, wherein said P protein has at least 40% identity to the amino acid sequence set forth in SEQ ID NO: 2.

33. The virus according to claim 16, wherein the mutation of an amino acid is a substitution to proline.

34. The virus according to claim 16, wherein the virus is a measles virus.

35. The virus according to claim 16, wherein the P protein further has an additional mutation of an amino acid at a position corresponding to the 110$^{th}$ and/or 275$^{th}$ position of a protein comprising the amino acid sequence set forth in SEQ ID NO: 2, wherein said additional mutation confers temperature-sensitivity on the virus.

36. The virus according to claim 35, wherein either or both additional mutation(s) is a substitution to tyrosine.

37. A pharmaceutical composition comprising the virus according to claim 32 and a pharmacologically acceptable carrier or medium.

38. A pharmaceutical composition comprising the virus according to claim 33 and a pharmacologically acceptable carrier or medium.

39. A pharmaceutical composition comprising the virus according to claim 34 and a pharmacologically acceptable carrier or medium.

40. A pharmaceutical composition comprising the virus according to claim 35 and a pharmacologically acceptable carrier or medium.

41. A pharmaceutical composition comprising the virus according to claim 36 and a pharmaceutically acceptable carrier or medium.

42. The polynucleotide according to claim 1, wherein said protein has at least 60% identity to the amino acid sequence set forth in SEQ ID NO: 2.

43. The polynucleotide according to claim 1, wherein said protein has at least 80% identity to the amino acid sequence set forth in SEQ ID NO: 2.

44. The Morbillivirus P protein according to claim 7, wherein said protein has at least 60% identity to the amino acid sequence set forth in SEQ ID NO: 2.

45. The Morbillivirus P protein according to claim 7, wherein said protein has at least 80% identity to the amino acid sequence set forth in SEQ ID NO: 2.

46. The method according to claim 10, wherein the Morbillivirus P protein has at least 60% identity to the amino acid sequence set forth in SEQ ID NO: 2.

47. The method according to claim 10, wherein the Morbillivirus P protein has at least 80% identity to the amino acid sequence set forth in SEQ ID NO: 2.

48. The method according to claim 26, wherein the Morbillivirus P protein has at least 60% identity to the amino acid sequence set forth in SEQ ID NO: 2.

49. The method according to claim 26, wherein the Morbillivirus P protein has at least 80% identity to the amino acid sequence set forth in SEQ ID NO: 2.

50. The virus according to claim 16, wherein said P protein has at least 60% identity to the amino acid sequence set forth in SEQ ID NO: 2.

51. The virus according to claim 16, wherein said P protein has at least 80% identity to the amino acid sequence set forth in SEQ ID NO: 2.

52. A pharmaceutical composition comprising the virus according to claim 50 and a pharmacologically acceptable carrier or medium.

53. A pharmaceutical composition comprising the virus according to claim 51 and a pharmacologically acceptable carrier or medium.

* * * * *

SEQUENCE LISTING

```
<160> NUMBER OF SEQ ID NOS: 6

<210> SEQ ID NO 1
<211> LENGTH: 2596
<212> TYPE: DNA
<213> ORGANISM: Measles virus
<220> FEATURE:
<221> NAME/KEY: CDS
<222> LOCATION: (60)..(1583)
<220> FEATURE:
<221> NAME/KEY: CDS
<222> LOCATION: (82)..(642)

<400> SEQUENCE: 1
aggaaccagg tccacacagc cgccagccca tcaaccatcc actcccacga ttggagccg      59 atg gca gaa gag cag gca cgc cat gtc aaa aac gga ctg gaa tgc atc     107
Met Ala Glu Glu Gln Ala Arg His Val Lys Asn Gly Leu Glu Cys Ile
  1               5                  10                  15 cgg gct ctc aag gcc gag ccc atc ggc tca ctg gcc atc gag gaa gct     155
Arg Ala Leu Lys Ala Glu Pro Ile Gly Ser Leu Ala Ile Glu Glu Ala
             20                  25                  30 atg gca gca tgg tca gaa ata tca gac aac cca gga cag gag cga gcc     203
Met Ala Ala Trp Ser Glu Ile Ser Asp Asn Pro Gly Gln Glu Arg Ala
         35                  40                  45 acc tgc agg gaa gag aag gca ggc agt tcg ggt ctc agc aaa cca tgc     251
Thr Cys Arg Glu Glu Lys Ala Gly Ser Ser Gly Leu Ser Lys Pro Cys
 50                  55                  60 ctc tca gca att gga tca act gaa ggc ggt gca cct cgc atc cgc ggt     299
Leu Ser Ala Ile Gly Ser Thr Glu Gly Gly Ala Pro Arg Ile Arg Gly
 65                  70                  75                  80 cag gga cct gga gag agc gat gac gac gct gaa act ttg gga atc ccc     347
Gln Gly Pro Gly Glu Ser Asp Asp Asp Ala Glu Thr Leu Gly Ile Pro
                 85                  90                  95 cca aga aat ctc cag gca tca agc act ggg tta cag tgt gat tat gtt     395
Pro Arg Asn Leu Gln Ala Ser Ser Thr Gly Leu Gln Cys Asp Tyr Val
            100                 105                 110 tat gat cac agc ggt gaa gcg gtt aag gga atc caa gat gct gac tct     443
Tyr Asp His Ser Gly Glu Ala Val Lys Gly Ile Gln Asp Ala Asp Ser
        115                 120                 125 atc atg gtt caa tca ggc ctt gat ggt gat agc acc ctc tca gga gga     491
Ile Met Val Gln Ser Gly Leu Asp Gly Asp Ser Thr Leu Ser Gly Gly
    130                 135                 140 gac aat gaa tct gaa aac agc gat gtg gat att ggc gaa cct gat acc     539
Asp Asn Glu Ser Glu Asn Ser Asp Val Asp Ile Gly Glu Pro Asp Thr
145                 150                 155                 160 gag gga tat gct atc act gac cgg gga tct gct ccc atc tct atg ggg     587
Glu Gly Tyr Ala Ile Thr Asp Arg Gly Ser Ala Pro Ile Ser Met Gly
                165                 170                 175
```

```
ttc agg gct tct gat gtt gaa act gca gaa gga ggg gag atc cac gag    635
Phe Arg Ala Ser Asp Val Glu Thr Ala Glu Gly Gly Glu Ile His Glu
            180                 185                 190 ctc ctg aga ctc caa tcc aga ggc aac aac ttt ccg aag ctt ggg aaa    683
Leu Leu Arg Leu Gln Ser Arg Gly Asn Asn Phe Pro Lys Leu Gly Lys
        195                 200                 205 act ctc aat gtt cct ccg ccc ccg gac ccc ggt agg gcc agc act tcc    731
Thr Leu Asn Val Pro Pro Pro Pro Asp Pro Gly Arg Ala Ser Thr Ser
    210                 215                 220 ggg aca ccc att aaa aag ggc aca gac gcg aga tta gcc tca ttt gga    779
Gly Thr Pro Ile Lys Lys Gly Thr Asp Ala Arg Leu Ala Ser Phe Gly
225                 230                 235                 240 acg gag atc gcg tct tta ttg aca ggt ggt gca acc caa tgt gct cga    827
Thr Glu Ile Ala Ser Leu Leu Thr Gly Gly Ala Thr Gln Cys Ala Arg
                245                 250                 255 aag tca ccc tcg gaa cca tca ggg cca ggt gca cct gcg ggg aat gtc    875
Lys Ser Pro Ser Glu Pro Ser Gly Pro Gly Ala Pro Ala Gly Asn Val
            260                 265                 270 ccc gag tgt gtg agc aat gcc gca ctg ata cag gag tgg aca ccc gaa    923
Pro Glu Cys Val Ser Asn Ala Ala Leu Ile Gln Glu Trp Thr Pro Glu
        275                 280                 285 tct ggt acc aca atc tcc ccg aga tcc cag aat aat gaa gaa ggg gga    971
Ser Gly Thr Thr Ile Ser Pro Arg Ser Gln Asn Asn Glu Glu Gly Gly
    290                 295                 300 gac tat tat gat gat gag ctg ttc tct gat gtc caa gat att aaa aca   1019
Asp Tyr Tyr Asp Asp Glu Leu Phe Ser Asp Val Gln Asp Ile Lys Thr
305                 310                 315                 320 gcc ttg gcc aaa ata cac gag gat aat cag aag ata atc tcc aag cta   1067
Ala Leu Ala Lys Ile His Glu Asp Asn Gln Lys Ile Ile Ser Lys Leu
                325                 330                 335 gaa tca ctg ctg tta ttg aag gga gaa gtt gag tca att aag aag cag   1115
Glu Ser Leu Leu Leu Leu Lys Gly Glu Val Glu Ser Ile Lys Lys Gln
            340                 345                 350 atc aac agg caa aat atc agc ata tcc acc ctg gaa gga cac ctc tca   1163
Ile Asn Arg Gln Asn Ile Ser Ile Ser Thr Leu Glu Gly His Leu Ser
        355                 360                 365 agc atc atg atc gcc att cct gga ctt ggg aag gat ccc aac gac ccc   1211
Ser Ile Met Ile Ala Ile Pro Gly Leu Gly Lys Asp Pro Asn Asp Pro
    370                 375                 380 act gca gat gtc gaa atc aat ccc gac ttg aaa ccc atc ata ggc aga   1259
Thr Ala Asp Val Glu Ile Asn Pro Asp Leu Lys Pro Ile Ile Gly Arg
385                 390                 395                 400 gat tca ggc cga gca ctg gcc gaa gtt ctc aag aaa ccc gtt gcc agc   1307
Asp Ser Gly Arg Ala Leu Ala Glu Val Leu Lys Lys Pro Val Ala Ser
                405                 410                 415 cga caa ctc caa gga atg aca aat gga cgg acc agt tcc aga gga cag   1355
Arg Gln Leu Gln Gly Met Thr Asn Gly Arg Thr Ser Ser Arg Gly Gln
            420                 425                 430 ctg ctg aag gaa ttt cag cta aag ccg atc ggg aaa aag atg agc tca   1403
Leu Leu Lys Glu Phe Gln Leu Lys Pro Ile Gly Lys Lys Met Ser Ser
        435                 440                 445 gcc gtc ggg ttt gtt cct gac acc ggc cct gca tca cgc agt gta atc   1451
Ala Val Gly Phe Val Pro Asp Thr Gly Pro Ala Ser Arg Ser Val Ile
    450                 455                 460 cgc tcc att ata aaa tcc agc cgg cta gag gag gat cgg aag cgt tac   1499
Arg Ser Ile Ile Lys Ser Ser Arg Leu Glu Glu Asp Arg Lys Arg Tyr
465                 470                 475                 480 ctg atg act ctc ctt gat gat atc aaa gga gcc aat gat ctt gcc aag   1547
Leu Met Thr Leu Leu Asp Asp Ile Lys Gly Ala Asn Asp Leu Ala Lys
```

-continued

```
                485                 490                 495
ttc cac cag atg ctg atg aag ata ata atg aag tag  gactccaatc        1593
Phe His Gln Met Leu Met Lys Ile Ile Met Lys
              500                 505 cagaggcaac aactttccga agcttgggaa aactctcaat gttcctccgc ccccggaccc   1653
cggtagggcc agcacttccg ggacacccat taaaagggc acagacgcga gattagcctc    1713
atttggaacg agatcgcgt ctttattgac aggtggtgca acccaatgtg ctcgaaagtc    1773
accctcggaa ccatcagggc caggtgcacc tgcgggaat gtccccgagt gtgtgagcaa    1833
tgccgcactg atacaggagt ggacacccga atctggtacc acaatctccc cgagatccca   1893
gaataatgaa aagggggag actattatga tgatgagctg ttctctgatg tccaagatat    1953
taaaacagcc ttggccaaaa tacacgagga taatcagaag ataatctcca agctagaatc   2013
actgctgtta ttgaagggag aagttgagtc aattaagaag cagatcaaca ggcaaaatat   2073
cagcatatcc accctggaag gacacctctc aagcatcatg atcgccattc ctggacttgg   2133
gaaggatccc aacgacccca ctgcagatgt cgaaatcaat cccgacttga acccatcat    2193 aggcagagat tcaggccgag cactggccga agttctcaag aaacccgttg ccagccgaca   2253
actccaagga atgacaaatg gacggaccag ttccagagga cagctgctga aggaatttca   2313
gctaaagccg atcgggaaaa agatgagctc agccgtcggg tttgttcctg acaccggccc   2373
tgcatcacgc agtgtaatcc gctccattat aaaatccagc cggctagagg aggatcggaa   2433
gcgttacctg atgactctcc ttgatgatat caaggagcc aatgatcttg ccaagttcca    2493
ccagatgctg atgaagataa taatgaagta gctacagctc aacttacctg ccaaccccat   2553
gccagtcgac ccaactagta caacctaaat ccattataaa aaa                     2596
```

<210> SEQ ID NO 2
<211> LENGTH: 507
<212> TYPE: PRT
<213> ORGANISM: Measles virus

<400> SEQUENCE: 2

```
Met Ala Glu Glu Gln Ala Arg His Val Lys Asn Gly Leu Glu Cys Ile
 1               5                  10                  15

Arg Ala Leu Lys Ala Glu Pro Ile Gly Ser Leu Ala Ile Glu Glu Ala
                20                  25                  30

Met Ala Ala Trp Ser Glu Ile Ser Asp Asn Pro Gly Gln Glu Arg Ala
            35                  40                  45

Thr Cys Arg Glu Glu Lys Ala Gly Ser Ser Gly Leu Ser Lys Pro Cys
        50                  55                  60

Leu Ser Ala Ile Gly Ser Thr Glu Gly Gly Ala Pro Arg Ile Arg Gly
    65                  70                  75                  80

Gln Gly Pro Gly Glu Ser Asp Asp Ala Glu Thr Leu Gly Ile Pro
                85                  90                  95

Pro Arg Asn Leu Gln Ala Ser Ser Thr Gly Leu Gln Cys Asp Tyr Val
               100                 105                 110

Tyr Asp His Ser Gly Glu Ala Val Lys Gly Ile Gln Asp Ala Asp Ser
            115                 120                 125

Ile Met Val Gln Ser Gly Leu Asp Gly Asp Ser Thr Leu Ser Gly Gly
        130                 135                 140

Asp Asn Glu Ser Glu Asn Ser Asp Val Asp Ile Gly Glu Pro Asp Thr
    145                 150                 155                 160

Glu Gly Tyr Ala Ile Thr Asp Arg Gly Ser Ala Pro Ile Ser Met Gly
```

```
                    165                 170                 175
Phe Arg Ala Ser Asp Val Glu Thr Ala Glu Gly Gly Glu Ile His Glu
                180                 185                 190
Leu Leu Arg Leu Gln Ser Arg Gly Asn Asn Phe Pro Lys Leu Gly Lys
            195                 200                 205
Thr Leu Asn Val Pro Pro Pro Asp Pro Gly Arg Ala Ser Thr Ser
        210                 215                 220
Gly Thr Pro Ile Lys Lys Gly Thr Asp Ala Arg Leu Ala Ser Phe Gly
225                 230                 235                 240
Thr Glu Ile Ala Ser Leu Leu Thr Gly Gly Ala Thr Gln Cys Ala Arg
                245                 250                 255
Lys Ser Pro Ser Glu Pro Ser Gly Pro Gly Ala Pro Ala Gly Asn Val
                260                 265                 270
Pro Glu Cys Val Ser Asn Ala Ala Leu Ile Gln Glu Trp Thr Pro Glu
            275                 280                 285
Ser Gly Thr Thr Ile Ser Pro Arg Ser Gln Asn Asn Glu Glu Gly Gly
        290                 295                 300
Asp Tyr Tyr Asp Asp Glu Leu Phe Ser Asp Val Gln Asp Ile Lys Thr
305                 310                 315                 320
Ala Leu Ala Lys Ile His Glu Asp Asn Gln Lys Ile Ile Ser Lys Leu
                325                 330                 335
Glu Ser Leu Leu Leu Leu Lys Gly Glu Val Glu Ser Ile Lys Lys Gln
                340                 345                 350
Ile Asn Arg Gln Asn Ile Ser Ile Ser Thr Leu Glu Gly His Leu Ser
            355                 360                 365
Ser Ile Met Ile Ala Ile Pro Gly Leu Gly Lys Asp Pro Asn Asp Pro
        370                 375                 380
Thr Ala Asp Val Glu Ile Asn Pro Asp Leu Lys Pro Ile Ile Gly Arg
385                 390                 395                 400
Asp Ser Gly Arg Ala Leu Ala Glu Val Leu Lys Lys Pro Val Ala Ser
                405                 410                 415
Arg Gln Leu Gln Gly Met Thr Asn Gly Arg Thr Ser Ser Arg Gly Gln
                420                 425                 430
Leu Leu Lys Glu Phe Gln Leu Lys Pro Ile Gly Lys Lys Met Ser Ser
            435                 440                 445
Ala Val Gly Phe Val Pro Asp Thr Gly Pro Ala Ser Arg Ser Val Ile
        450                 455                 460
Arg Ser Ile Ile Lys Ser Ser Arg Leu Glu Glu Asp Arg Lys Arg Tyr
465                 470                 475                 480
Leu Met Thr Leu Leu Asp Asp Ile Lys Gly Ala Asn Asp Leu Ala Lys
                485                 490                 495
Phe His Gln Met Leu Met Lys Ile Ile Met Lys
                500                 505

<210> SEQ ID NO 3
<211> LENGTH: 186
<212> TYPE: PRT
<213> ORGANISM: Measles virus

<400> SEQUENCE: 3

Met Ser Lys Thr Asp Trp Asn Ala Ser Gly Leu Ser Arg Pro Ser Pro
  1               5                  10                  15

Ser Ala His Trp Pro Ser Arg Lys Leu Trp Gln His Gly Gln Lys Tyr
                 20                  25                  30
```

|  |  |  |  |  |  |  |  |  |  |  |  |  |
|---|---|---|---|---|---|---|---|---|---|---|---|---|
| Gln | Thr | Thr | Gln | Asp | Arg | Ser | Glu | Pro | Pro | Ala | Gly | Lys | Arg | Arg | Gln |
|  |  | 35 |  |  |  | 40 |  |  |  | 45 |  |  |  |

Ala Val Arg Val Ser Ala Asn His Ala Ser Gln Gln Leu Asp Gln Leu
            50                  55                  60

Lys Ala Val His Leu Ala Ser Ala Val Arg Asp Leu Glu Arg Ala Met
65              70                  75                  80

Thr Thr Leu Lys Leu Trp Glu Ser Pro Gln Glu Ile Ser Arg His Gln
                85                  90                  95

Ala Leu Gly Tyr Ser Val Ile Met Phe Met Ile Thr Ala Val Lys Arg
            100                 105                 110

Leu Arg Glu Ser Lys Met Leu Thr Leu Ser Trp Phe Asn Gln Ala Leu
        115                 120                 125

Met Val Ile Ala Pro Ser Gln Glu Thr Met Asn Leu Lys Thr Ala
    130                 135                 140

Met Trp Ile Leu Ala Asn Leu Ile Pro Arg Asp Met Leu Ser Leu Thr
145                 150                 155                 160

Gly Asp Leu Leu Pro Ser Leu Trp Gly Ser Gly Leu Leu Met Leu Lys
                165                 170                 175

Leu Gln Lys Glu Gly Arg Ser Thr Ser Ser
            180                 185

<210> SEQ ID NO 4
<211> LENGTH: 2596
<212> TYPE: DNA
<213> ORGANISM: Measles virus
<220> FEATURE:
<221> NAME/KEY: CDS
<222>

```
Ile Met Val Gln Ser Gly Leu Asp Gly Asp Ser Thr Leu Ser Gly Gly
    130                 135                 140 gac aat gaa tct gaa aac agc gat gtg gat att ggc gaa cct gat acc    539
Asp Asn Glu Ser Glu Asn Ser Asp Val Asp Ile Gly Glu Pro Asp Thr
145                 150                 155                 160 gag gga tat gct atc act gac cgg gga tct gct ccc atc tct atg ggg    587
Glu Gly Tyr Ala Ile Thr Asp Arg Gly Ser Ala Pro Ile Ser Met Gly
                165                 170                 175 ttc agg gct tct gat gtt gaa act gca gaa gga ggg gag atc cac gag    635
Phe Arg Ala Ser Asp Val Glu Thr Ala Glu Gly Gly Glu Ile His Glu
            180                 185                 190 ctc ctg aga ctc caa tcc aga ggc aac aac ttt ccg aag ctt ggg aaa    683
Leu Leu Arg Leu Gln Ser Arg Gly Asn Asn Phe Pro Lys Leu Gly Lys
        195                 200                 205 act ctc aat gtt cct ccg ccc ccg gac ccc ggt agg gcc agc act tcc    731
Thr Leu Asn Val Pro Pro Pro Pro Asp Pro Gly Arg Ala Ser Thr Ser
    210                 215                 220 ggg aca ccc att aaa aag ggc aca gac gcg aga tta gcc tca ttt gga    779
Gly Thr Pro Ile Lys Lys Gly Thr Asp Ala Arg Leu Ala Ser Phe Gly
225                 230                 235                 240 acg gag atc gcg tct tta ttg aca ggt ggt gca acc caa tgt gct cga    827
Thr Glu Ile Ala Ser Leu Leu Thr Gly Gly Ala Thr Gln Cys Ala Arg
                245                 250                 255 aag tca ccc tcg gaa cca tca ggg cca ggt gca cct gcg ggg aat gtc    875
Lys Ser Pro Ser Glu Pro Ser Gly Pro Gly Ala Pro Ala Gly Asn Val
            260                 265                 270 ccc gag tat gtg agc aat gcc gca ctg ata cag gag tgg aca ccc gaa    923
Pro Glu Tyr Val Ser Asn Ala Ala Leu Ile Gln Glu Trp Thr Pro Glu
        275                 280                 285 tct ggt acc aca atc tcc ccg aga tcc cag aat aat gaa gaa ggg gga    971
Ser Gly Thr Thr Ile Ser Pro Arg Ser Gln Asn Asn Glu Glu Gly Gly
    290                 295                 300 gac tat tat gat gat gag ctg ttc tct gat gtc caa gat att aaa aca   1019
Asp Tyr Tyr Asp Asp Glu Leu Phe Ser Asp Val Gln Asp Ile Lys Thr
305                 310                 315                 320 gcc ttg gcc aaa ata cac gag gat aat cag aag ata atc tcc aag cta   1067
Ala Leu Ala Lys Ile His Glu Asp Asn Gln Lys Ile Ile Ser Lys Leu
                325                 330                 335 gaa tca ctg ctg tta ttg aag gga gaa gtt gag tca att aag aag cag   1115
Glu Ser Leu Leu Leu Leu Lys Gly Glu Val Glu Ser Ile Lys Lys Gln
            340                 345                 350 atc aac agg caa aat atc agc ata tcc acc ctg gaa gga cac ctc tca   1163
Ile Asn Arg Gln Asn Ile Ser Ile Ser Thr Leu Glu Gly His Leu Ser
        355                 360                 365 agc atc atg atc gcc att cct gga ctt ggg aag gat ccc aac gac ccc   1211
Ser Ile Met Ile Ala Ile Pro Gly Leu Gly Lys Asp Pro Asn Asp Pro
    370                 375                 380 act gca gat gtc gaa atc aat ccc gac ttg aaa ccc atc ata ggc aga   1259
Thr Ala Asp Val Glu Ile Asn Pro Asp Leu Lys Pro Ile Ile Gly Arg
385                 390                 395                 400 gat tca ggc cga gca ctg gcc gaa gtt ctc aag aaa ccc gtt gcc agc   1307
Asp Ser Gly Arg Ala Leu Ala Glu Val Leu Lys Lys Pro Val Ala Ser
                405                 410                 415 cga caa ctc caa gga atg aca aat gga cgg acc agt tcc aga gga cag   1355
Arg Gln Leu Gln Gly Met Thr Asn Gly Arg Thr Ser Ser Arg Gly Gln
            420                 425                 430 ctg ctg aag gaa ttt cag cca aag ccg atc ggg aaa aag atg agc tca   1403
Leu Leu Lys Glu Phe Gln Pro Lys Pro Ile Gly Lys Lys Met Ser Ser
        435                 440                 445
```

```
gcc gtc ggg ttt gtt cct gac acc ggc cct gca tca cgc agt gta atc    1451
Ala Val Gly Phe Val Pro Asp Thr Gly Pro Ala Ser Arg Ser Val Ile
450                 455                 460 cgc tcc att ata aaa tcc agc cgg cta gag gag gat cgg aag cgt tac    1499
Arg Ser Ile Ile Lys Ser Ser Arg Leu Glu Glu Asp Arg Lys Arg Tyr
465                 470                 475                 480 ctg atg act ctc ctt gat gat atc aaa gga gcc aat gat ctt gcc aag    1547
Leu Met Thr Leu Leu Asp Asp Ile Lys Gly Ala Asn Asp Leu Ala Lys
            485                 490                 495 ttc cac cag atg ctg atg aag ata ata atg aag tag  gactccaatc       1593
Phe His Gln Met Leu Met Lys Ile Ile Met Lys
                500                 505 cagaggcaac aactttccga agcttgggaa aactctcaat gttcctccgc ccccggaccc   1653
cggtagggcc agcacttccg ggacacccat taaaagggc acagacgcga gattagcctc   1713
atttggaacg agatcgcgt ctttattgac aggtggtgca acccaatgtg ctcgaaagtc   1773
accctcggaa ccatcagggc caggtgcacc tgcgggaat gtccccgagt atgtgagcaa    1833
tgccgcactg atacaggagt ggacacccga atctggtacc acaatctccc cgagatccca   1893
gaataatgaa aaggggag actattatga tgatgagctg ttctctgatg tccaagatat    1953
taaaacagcc ttggccaaaa tacacgagga taatcagaag ataatctcca gctagaatc    2013
actgctgtta ttgaagggag aagttgagtc aattaagaag cagatcaaca ggcaaaatat   2073
cagcatatcc accctggaag gacacctctc aagcatcatg atcgccattc ctggacttgg   2133
gaaggatccc aacgacccca ctgcagatgt cgaaatcaat cccgacttga aacccatcat   2193
aggcagagat tcaggccgag cactggccga gttctcaag aaacccgttg ccagccgaca    2253
actccaagga atgacaaatg gacggaccag ttccagagga cagctgctga aggaatttca   2313
gccaaagccg atcgggaaaa agatgagctc agccgtcggg tttgttcctg acaccggccc   2373
tgcatcacgc agtgtaatcc gctccattat aaaatccagc cggctagagg aggatcggaa   2433
gcgttacctg atgactctcc ttgatgatat caaaggagcc aatgatcttg ccaagttcca   2493
ccagatgctg atgaagataa taatgaagta gctacagctc aacttacctg ccaacccccat   2553
gccagtcgac ccaactagta caacctaaat ccattataaa aaa                    2596
```

<210> SEQ ID NO 5
<211> LENGTH: 507
<212> TYPE: PRT
<213> ORGANISM: Measles virus

<400> SEQUENCE: 5

```
Met Ala Glu Glu Gln Ala Arg His Val Lys Asn Gly Leu Glu Cys Ile
1               5                   10                  15

Arg Ala Leu Lys Ala Glu Pro Ile Gly Ser Leu Ala Ile Glu Glu Ala
            20                  25                  30

Met Ala Ala Trp Ser Glu Ile Ser Asp Asn Pro Gly Gln Glu Arg Ala
        35                  40                  45

Thr Cys Arg Glu Glu Lys Ala Gly Ser Ser Gly Leu Ser Lys Pro Cys
    50                  55                  60

Leu Ser Ala Ile Gly Ser Thr Glu Gly Gly Ala Pro Arg Ile Arg Gly
65                  70                  75                  80

Gln Gly Pro Gly Glu Ser Asp Asp Ala Glu Thr Leu Gly Ile Pro
                85                  90                  95

Pro Arg Asn Leu Gln Ala Ser Ser Thr Gly Leu Gln Cys Tyr Tyr Val
                100                 105                 110
```

```
Tyr Asp His Ser Gly Glu Ala Val Lys Gly Ile Gln Asp Ala Asp Ser
        115                 120                 125
Ile Met Val Gln Ser Gly Leu Asp Gly Asp Ser Thr Leu Ser Gly Gly
    130                 135                 140
Asp Asn Glu Ser Glu Asn Ser Asp Val Asp Ile Gly Glu Pro Asp Thr
145                 150                 155                 160
Glu Gly Tyr Ala Ile Thr Asp Arg Gly Ser Ala Pro Ile Ser Met Gly
                165                 170                 175
Phe Arg Ala Ser Asp Val Glu Thr Ala Glu Gly Gly Glu Ile His Glu
            180                 185                 190
Leu Leu Arg Leu Gln Ser Arg Gly Asn Asn Phe Pro Lys Leu Gly Lys
        195                 200                 205
Thr Leu Asn Val Pro Pro Pro Asp Pro Gly Arg Ala Ser Thr Ser
    210                 215                 220
Gly Thr Pro Ile Lys Lys Gly Thr Asp Ala Arg Leu Ala Ser Phe Gly
225                 230                 235                 240
Thr Glu Ile Ala Ser Leu Leu Thr Gly Gly Ala Thr Gln Cys Ala Arg
                245                 250                 255
Lys Ser Pro Ser Glu Pro Ser Gly Pro Gly Ala Pro Ala Gly Asn Val
            260                 265                 270
Pro Glu Tyr Val Ser Asn Ala Ala Leu Ile Gln Glu Trp Thr Pro Glu
        275                 280                 285
Ser Gly Thr Thr Ile Ser Pro Arg Ser Gln Asn Asn Glu Glu Gly Gly
    290                 295                 300
Asp Tyr Tyr Asp Asp Glu Leu Phe Ser Asp Val Gln Asp Ile Lys Thr
305                 310                 315                 320
Ala Leu Ala Lys Ile His Glu Asp Asn Gln Lys Ile Ile Ser Lys Leu
                325                 330                 335
Glu Ser Leu Leu Leu Leu Lys Gly Glu Val Glu Ser Ile Lys Lys Gln
            340                 345                 350
Ile Asn Arg Gln Asn Ile Ser Ile Ser Thr Leu Glu Gly His Leu Ser
        355                 360                 365
Ser Ile Met Ile Ala Ile Pro Gly Leu Gly Lys Asp Pro Asn Asp Pro
    370                 375                 380
Thr Ala Asp Val Glu Ile Asn Pro Asp Leu Lys Pro Ile Ile Gly Arg
385                 390                 395                 400
Asp Ser Gly Arg Ala Leu Ala Glu Val Leu Lys Lys Pro Val Ala Ser
                405                 410                 415
Arg Gln Leu Gln Gly Met Thr Asn Gly Arg Thr Ser Ser Arg Gly Gln
            420                 425                 430
Leu Leu Lys Glu Phe Gln Pro Lys Pro Ile Gly Lys Lys Met Ser Ser
        435                 440                 445
Ala Val Gly Phe Val Pro Asp Thr Gly Pro Ala Ser Arg Ser Val Ile
    450                 455                 460
Arg Ser Ile Ile Lys Ser Ser Arg Leu Glu Glu Asp Arg Lys Arg Tyr
465                 470                 475                 480
Leu Met Thr Leu Leu Asp Asp Ile Lys Gly Ala Asn Asp Leu Ala Lys
                485                 490                 495
Phe His Gln Met Leu Met Lys Ile Ile Met Lys
            500                 505

<210> SEQ ID NO 6
<211> LENGTH: 186
<212> TYPE: PRT
```

```
<213> ORGANISM: Measles virus

<400> SEQUENCE: 6

Met Ser Lys Thr Asp Trp Asn Ala Ser Gly Leu Ser Arg Pro Ser Pro
 1               5                  10                  15

Ser Ala His Trp Pro Ser Arg Lys Leu Trp Gln His Gly Gln Lys Tyr
                20                  25                  30

Gln Thr Thr Gln Asp Arg Ser Glu Pro Pro Ala Gly Lys Arg Arg Gln
            35                  40                  45

Ala Val Arg Val Ser Ala Asn His Ala Ser Gln Gln Leu Asp Gln Leu
        50                  55                  60

Lys Ala Val His Leu Ala Ser Ala Val Arg Asp Leu Glu Arg Ala Met
 65                  70                  75                  80

Thr Thr Leu Lys Leu Trp Glu Ser Pro Gln Glu Ile Ser Arg His Gln
                85                  90                  95

Ala Leu Gly Tyr Ser Val Ile Met Phe Met Ile Thr Ala Val Lys Arg
            100                 105                 110

Leu Arg Glu Ser Lys Met Leu Thr Leu Ser Trp Phe Asn Gln Ala Leu
            115                 120                 125

Met Val Ile Ala Pro Tyr Gln Glu Glu Thr Met Asn Leu Lys Thr Ala
    130                 135                 140

Met Trp Ile Leu Ala Asn Leu Ile Pro Arg Asp Met Leu Ser Leu Thr
145                 150                 155                 160

Gly Asp Leu Leu Pro Ser Leu Trp Gly Ser Gly Leu Leu Met Leu Lys
                165                 170                 175

Leu Gln Lys Glu Gly Arg Ser Thr Ser Ser
                180                 185
```